US007838216B1

(12) United States Patent
King et al.

(10) Patent No.: US 7,838,216 B1
(45) Date of Patent: Nov. 23, 2010

(54) HUMAN GENE RELATED TO BUT DISTINCT FROM EGF RECEPTOR GENE

(75) Inventors: C. Richter King, Washington, DC (US); Matthias H. Kraus, Bethesda, MD (US); Stuart A. Aaronson, Great Falls, VA (US)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 07/110,791

(22) Filed: Oct. 21, 1987

Related U.S. Application Data

(63) Continuation-in-part of application No. 06/836,414, filed on Mar. 5, 1986, now abandoned.

(51) Int. Cl.
C12Q 1/68 (2006.01)
(52) U.S. Cl. ...................... 435/6; 536/23.5; 536/24.31; 530/350; 530/387.1; 530/387.7; 530/387.9; 435/7.1; 436/64
(58) Field of Classification Search .................... 435/6, 435/7, 91, 172.3, 805, 810, 7.1, 7.21, 7.23; 436/501, 813, 64; 536/27, 23.1, 23.5, 24.3, 536/24.31; 935/9, 19, 29, 78; 530/387.7, 530/350, 387.1, 387.9
See application file for complete search history.

(56) References Cited

U.S. PATENT DOCUMENTS 4,968,603 A * 11/1990 Slamon et al. ................. 435/6

OTHER PUBLICATIONS

Sedlak (1994) Genetic Engineering News of May 15, 1994, pp. 8-9.*
Brison (1993) Biochimica et Biophysica Acta, vol. 1155, pp. 25-41.*
Semba et al. (1985) Proc. Natl Acal Sci (USA), vol. 82, pp. 6497-6501.*
Yamamoto et al. (1986) Nature, vol. 319, pp. 230-234.*
Southern (J. Mol. Biol. Nov. 5, 1975; 98 (3): 503-517).*
Bergmann et al. (J. Virol. Sep. 1980;35 (3): 968-971).*
Coussens et al. (Science. Dec. 6, 1985; 230: 1132-1139).*
Scott et al. (Mol. Cell. Biol. Apr. 1993; 13 (4): 2247-2257).*
Aigner et al. (Oncogene. Apr. 19, 2001; 20 (17): 2101-2111).*
Doherty et al. (Proc. Natl. Acad. Sci. U S A. Sep. 14, 1999; 96 (19): 10869-10874).*
Koletsa et al. (Neoplasia. Jul. 2008; 10 (7): 687-696).*
Harris et al. (J. Am. Soc. Nephrol. 1995; 6: 1125-1133).*
Ahn et al. (Nature Gen. 1993; 3: 283-291).*
Cawthon et al. (Genomics 1991; 9: 446-460).*
Ward (Developmental Oncology 1985; 21: 91-106).*
Yokata et al. (Lancet. Apr. 5, 1986; 1 (8484): 765-767).*
Critchfield (Disease Markers 1999; 15: 108-111).*
Sidransky (Science 1997; 278: 1054-1058).*
Tockman et al. (Cancer Research 1992; 52: 2711s-2718s).*
Slamon et al. (Science. Jan. 9, 1987; 235: 177-182).*
Kim et al. (J. Korean Med. Sci. Jun. 2008; 23 (3): 414-420).*
Roessler et al. (Mol. Cell. Prot. 2006; 5 (11): 2092-2101).*
Roessler et al. (Clin. Can. Res. 2005; 11 (18): 6550-6557).*
Zolg et al. (Mol. Cell. Prot. 2004; 3 (4): 345-354).*
Leitzel et al. (J. Clin. Oncol. Sep. 1992; 10 (9): 1436-1443).*
Kath et al. (Ann. Oncol. Aug. 1993; 4 (7): 585-590).*
King et al. (Science. Sep. 6, 1985; 229: 974-976).*
Semba et al. (Proc. Natl. Acad. Sci. USA. Oct. 1985; 82: 6497-6501).*
Montgomery et al. (Proc. Natl. Acad Sci. U S A. Sep. 1983; 80 (18): 5724-5728).*
Brison et al. (Biochim. Biophys. Acta. May 25, 1993; 1155 (1): 25-41).*
Kozbor et al. (Cancer Res. Feb. 1984; 44 (2): 438-441).*
Filmus et al. (Biochem. Biophys. Res. Commun. Apr. 30, 1985; 128 (2): 898-905).*
Yander et al. (Cancer Res. Sep; 45 (9): 4433-4438).*
Kohl et al. (Cell. Dec. 1983; 35 (Pt 1): 359-367).*
Land et al., *Science* 222:771-778, 1983.
Cohen, et al., *J. Biol. Chem* 255:4834-4842, 1980.
Nishimura, et al. *Proc. Natl. Acad. Sci. USA* 79:4303-4307, 1982.
Kasuga et al. *Nature* 298:667-669, 1982.
Rubin, et al. *Nature* 305:438-440, 1983.
Yamamoto, et al. *Cell* 35:71-78, 1983.
de Klein, et al., *Nature* 300:765, 1982.
Collins, et al. *Proc. Natl. Acad. Sci. USA* 80:4813, 1983.
Liberman, et al., *Nature* 313:144, 1985.
Lin, et al. *Science* 224:843, 1984.
Rigby, et al., *J. Mol. Biol.* 113:237, 1977.
Wahl, et al. *Proc. Natl. Acad. Sci USA* 76:3683-3687, 1979.
Downward, et al. *Nature* 307:521-527, 1984.
Ullrich, et al., *Nature* 309:418-425, 1984.
Doolittle, et al. *Science* 221:275-277, 1983.
King et al., Amplification of a Novel v-erbB-Related Gene in a Human Mammary Carcinoma, *Science*, (1985) 229:974-976.
Kraus et al., Overexpression of the EGF Receptor-Related Proto-Oncogene erbB-2 in Human Mammary Tumor Cell Lines . . . *The EMBO Journal*, (1987) 6:605-610.
Di Foire et al., erbB-2 Is A Potent Oncogene when Overexpressed in NIH/3T3 Cells, *Science.*,(1987) 237:178-182.
Lacroix et al., Overexpression of erbB-2 or EGF Receptor Proteins Present In Early Stage Mammary . . . *Oncogene*, (1989) 4:145-151.
Slamon et al., Human Breast Cancer: Correlation of Relapse and Survival with . . . , *Science*, (1987), 235:177-182.
A. Ullrich et al., "Human epidermal growth factor receptor cDNA sequence and aberrant expression of the amplified gene in A431 epidermoid carcinoma cells," Nature (1984) vol. 309, pp. 418-425.
Paik, S. et al. "Pathologic Findings From the National Surgical Adjuvant Breast and Bowel Project: Prognostic Significance of erbB-2 Protein Overexpression in Primary Breast Cancer" J. of Clinical Oncology (1990) 8:103-112.

(Continued)

*Primary Examiner*—Stephen L Rawlings
(74) *Attorney, Agent, or Firm*—Sheridan Ross P.C.; Susan S. Rucker

(57) ABSTRACT

The isolation, cloning and characterization of a human gene related to but distinct from EGF receptor gene has been described. Nucleotide sequence of the gene and amino acid sequence of the polypeptide encoded by the gene have been determined. The use of the nucleic acid probes and antibodies having specific binding affinity with said polypeptide for diagnostic and therapeutic purposes have also been described.

15 Claims, 10 Drawing Sheets

OTHER PUBLICATIONS

King, C.R. et al. "Heterogeneous Expression of erbB-2 Messenger RNA in Human Breast Cancer" Cancer Research(1989) 49:4185-4191.

Park, J-B. et al. "Amplification, Overexpression, and Rearrangement of erbB-2 Protooncogene in Primary Human Stomach Carcinomas" Cancer Research (1989) 49:6605-6609.

King, C.R. et al. "Implications of erbB-2 overexpression for basic science and clinical medicine" seminars in Cancer Biology (1990) 1:329-337.

Berger. M.S. et al. "Correlation of c-erbB-2 Gene Amplification and Protein Expression in Human Breast Carcinoma with Nodal Status and Nuclear Grading" Cancer Research (1988) 48:1238-1243.

* cited by examiner

US 7,838,216 B1

HUMAN GENE RELATED TO BUT DISTINCT FROM EGF RECEPTOR GENE

This application is a Continuation-in-Part of U.S. application Ser. No. 06/836,414 filed Mar. 5, 1986 now abandoned.

REFERENCE TO SEQUENCE LISTING

This application contains a Sequence Listing submitted as an electronic text file named "6137NCI-24_seq_listing_ST25.txt", having a size in bytes of 32KB, and created on Dec. 4, 2009. The information contained in this electronic file is hereby incorporated by reference in its entirety pursuant to 37 CFR §1.52(e)(5).

BACKGROUND OF THE INVENTION

1. Technical Field

The present invention is related to the cloning, isolation and partial characterization of a hitherto unidentified human gene. More particularly, the present invention is related to the preparation and identification of a v-erbB related human gene that is a new member of the tyrosine kinase encoding family of genes and is amplified in a human mammary carcinoma.

2. State of the Art

A number of genes have been identified as retroviral oncogenes that are responsible for inducing tumors in vivo and transforming cells in vitro (Land et al., Science 222:771-778, 1983). Some of them apparently encode transforming proteins that share a kinase domain homologous to that of pp60$^{src}$, a tyrosine-specific protein kinase. The cellular cognate, encoded by the c-src gene, also exhibits tyrosine-specific kinase activity. Of particular interest is the fact that tyrosine-specific kinases are also encoded by other genes for several receptors for polypeptide growth factors, including the receptors for epidermal growth factor (EGF) (Cohen et al., J. Biol. Chem. 255:4834-4842, 1980), platelet-derived growth factor (PDGF) (Nishimura et al., Proc. Natl. Acad. Sci. USA 79:4303-4307, 1982), insulin (Kasuga et al., Nature 298:667-669, 1982), and insulin-like growth factor I (Rubin et al., Nature 305:438-440, 1983). This implies a possible link between the action of the growth factor-receptor complex and the oncogene products with tyrosine-specific kinase activity.

Recent analysis of the v-erbB gene and the EGF receptor gene indicates that the v-erbB gene is a part of the EGF receptor gene and codes for the internal domain and transmembrane portion of the receptor (Yamamoto et al., Cell 35:71-78, 1983; Downward et al., Nature 307:521-527, 1984; Ullrich et al., Nature 309:418-425, 1984). These findings, together with the extensive identity of the amino acid sequences of the v-sis protein and platelet-derived growth factor (Waterfield et al., Nature 304:35-39, 1983; Doolittle et al., Science 221:275-277, 1983), suggest that some viral oncogene products mimic the action of the polypeptide growth factor-receptor complex in activating a cellular pathway involved in cell proliferation and tumor formation.

Genetic alterations affecting proto-oncogenes of the tyrosine kinase family may play a role in spontaneous tumor development. A specific translocation affecting the c-abl locus, for example, is associated with chronic myelogenous leukemia (de Klein et al., Nature 300:765, 1982; Collins et al., Proc. Natl. Acad. Sci. USA 80:4813, 1983). Several recent studies have also documented amplification or rearrangement of the gene for the EGF receptor in certain human tumors (Libermann et al., Nature 313:144, 1985), or tumor cell lines (Ullrich et al., Nature 309:418, 1984; Lin et al., Science 224:843, 1984). However, a gene that is a new member of the tyrosine kinase family and is amplified in a human mammary carcinoma and is closely related to, but distinct from the EGF receptor gene, has not heretofore been known.

SUMMARY OF THE INVENTION

It is, therefore, an object of the present invention to provide a novel, cloned, human gene having the nucleotide sequence as shown in FIG. 1 and described more fully herein infra.

It is a further object of the present invention to provide products, e.g. various RNAs and/or polypeptides encoded by the cloned gene.

It is a still further object of the present invention to provide antibodies, either polyclonal or monoclonal, directed against the protein product encoded by said gene and a diagnostic kit containing said antibodies for the detection of carcinomas.

It is another object of the present invention to provide complementary DNA (cDNA) clones homologous to the messenger RNA (mRNA) encoded by the cloned gene, said cDNA clones being capable of expressing large amounts of corresponding protein in a heterologous vector system, such as bacteria, yeast, eukaryotes and the like.

It is yet another object of the present invention to produce a transformed cell or organism capable of expressing said gene by incorporating said gene or a part thereof into the genome of said cell, vector or organism.

It is a still further object of the present invention to provide nucleic acid probes and/or antibody reagent kits capable of detecting said gene or a product thereof.

Other objects and advantages of the present invention will become apparent as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein.

Figure 1:
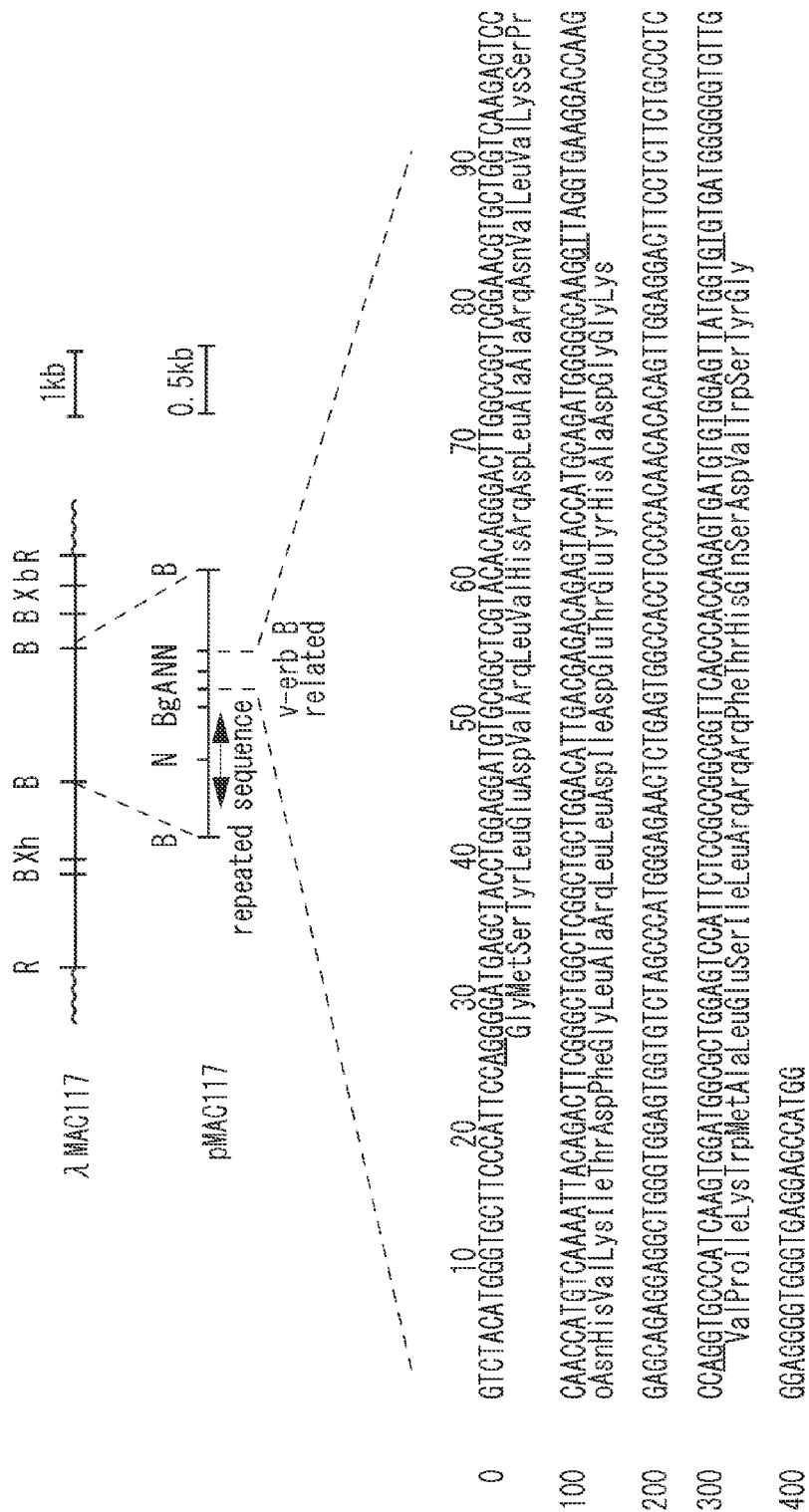
FIG. 1 shows a characteristic fragment produced by Eco RI restriction of the cloned gene of the present invention (identified as λMAC117, with the straight line representing the Eco RI fragment); a Bam HI fragment of λMAC117 which was subcloned into pUC12 (identified as pMAC117, with the straight line representing the Bam HI fragment); and the nucleic acid sequence of a DNA fragment flanked by Acc I and Nco I sites that hybridized with v-erbB probes. The nucleic acid sequence is represented by SEQ ID NO:2 and the amino acid sequence encoded thereby is represented by SEQ ID NO:1. The figure also shows restriction sites within the respective Eco RI and Bam HI fragments. A: Acc I; B: Bam HI; Bg: Bgl I; N: Nco I; R: Eco RI; X: Xba I; Xh: Xho I. The sites were located by electrophoretic analysis of the products of single and double digestion. Regions homologous to v-erbB or human repetitive sequences (region flanked by arrows) were located by Southern blot hybridization (Southern, J. Mol. Biol. 98:503 (1975)), with the v-erbB probe or total human DNA made radioactive by nick translation (Rigby et al., J. Mol. Biol. 113:237 (1977)). Hybridization conditions were as described in FIG. 2. The AG or GT dinucleotides flanking the putative coding regions are underlined. To determine the sequence, Nco I, Hinf I and Sau 96 I fragments were labeled at the 3' termini by means of a large fragment of E. coli DNA polymerase, separated into single strands by gel electrophoresis and chemically degraded (Maxam et al., Proc. Natl. Acad. Sci., USA 74:560 (1977)).

As disclosed in Ullrich et al. (1984), the nucleotide sequence of the EGF receptor gene is represented by SEQ ID NO:3 as follows:

GCCGCGCTGCGCCGGACTC-CCGAGCTAGCCCCGGCGCCGCCGCCGC-CCAGACCGGAC GACAGGCCACCTCGTCGGCGTC-CGCCCGAGTCCCCGCCTCGCCGCCAACGCCACAAC CACCGCGCACGGCCCCCTGACTCCGTC-CAGTATTGA

TCGGGAGAGCCGGAGCGAGCTCTTCGGG-GAGCAGCGATGCGACCCTCCGGGACGGC CGGGGCAGCGCTCCTGGCGCTGCTGGCT-GCGCTCTGCCCGGCGAGTCGGGCTCTG-GAGGAAAA

ACGCAGTTGGGCACTTTTGAAGAT-CATTTTCTCAGCCTCCAGAGGATGTTCAATAACT GTGAGGTGGTCCTTGGGAATTTGGAAAT-TACCTATGTGCAGAGGAATTATGATCTTT CCTTCT-TAAAGACCATCCAGGAGGTGGCTGGTTAT

GTCCTCATTGCCCTCAACACAGTGGAGC-GAATTCCTTTGGAAAACCTGCAGATCATC AGAG-GAAATATGTACTACGAAAATTCCTATGC-CTTAGCAGTCTTATCTAACTATGATG CAAATAAAACCGGACTGAAGGAGCTGCCCATGAGA

AATTTACAGGAAATCCTGCATGGCGC-CGTGCGGTTCAGCAACAACCCTGCCCTGTGC AACGTGGAGAGCATCCAGTGGCGGGA-CATAGTCAGCAGTGACTTTCTCAGCAACATG TCGATGGACTTCCAGAACCAC-CTGGGCAGCTGCCAA

AAGTGTGATCCAAGCTGTCCCAATGG-GAGCTGCTGGGGTGCAGGAGAGGAGAACTG CCA-GAAACTGACCAAAATCATCTGTGCCCAG-CAGTGCTCCGGGCGCTGCCGTGGCAA GTCCCCCAGTGACTGCTGCCACAAC-CAGTGTGCTGCA

GGCTGCACAGGCCCCCGGGAGAGCGACT-GCCTGGTCTGCCGCAAATTCCGAGACGAA GCCACGTGCAAGGACACCTGC-CCCCCACTCATGCTCTACAACCCCACCACGTACCAG ATGGATGTGAACCCCGAGGGCAAATA-CAGCTTTGGT

GCCACCTGCGTGAAGAAGTGTCCCCG-TAATTATGTGGTGACAGATCACGGCTCGTGC GTC-CGAGCCTGTGGGGCCGACAGCTAT-GAGATGGAGGAAGACGGCGTCCGCAAGTG TAAGAAGTGCGAAGGGCCTTGCCG-CAAAGTGTGTAAC

GGAATAGGTATTGGTGAATTTAAAGACT-CACTCTCCATAAATGCTACGAATATTAAA CACT-TCAAAAACTGCACCTCCATCAGTGGC-GATCTCCACATCCTGCCGGTGGCATTTA GGGGTGACTCCTTCACACATACTCCTCCTCTGGAT

CCACAGGAACTGGATATTCTGAAAACCG-TAAAGGAAATCACAGGGTTTTTGCTGATT CAGGCT-TGGCCTGAAAACAGGACGGACCTCCAT-GCCTTTGAGAACCTAGAAATCATA CGCGGCAGGACCAAGCAACATGGT-CAGTTTTCTCTT

GCAGTCGTCAGCCTGAACATAACATCCT-TGGGATTACGCTCCCTCAAGGAGATAAGT GATG-GAGATGTGATAATTTCAGGAAA-CAAAAATTTGTGCTATGCAAATACAATAAAC TGGAAAAAACTGTTTGGGACCTCCGGT-CAGAAAACC

AAAATTATAAGCAACAGAGGTGAAAA-CAGCTGCAAGGCCACAGGCCAGGTCTGCCA TGC-CTTGTGCTCCCCCGAGGGCTGCTGGGGC-CCGGAGCCCAGGGACTGCGTCTCTTG CCGGAATGTCAGCCGAGGCAGGGAAT-GCGTGGACAAG

TGCAAGCTTCTGGAGGGTGAGCCAAGG-GAGTTTGTGGAGAACTCTGAGTGCATACAG TGC-CACCCAGAGTGCCTGCCTCAGGCCAT-GAACATCACCTGCACAGGACGGGGACCAGACAAC

CCCCACTGCGTCAAGACCTGCCCGGCAG-GAGTCATGGGAGAAAACAACACCCTGGTC TGGAAGTACGCAGACGCCGGCCATGTGT-GCCACCTGTGCCATCCAAACTGCACCTAC GGATG-CACTGGGCCAGGTCTTGAAGGCTGTCCAACG

AATGGGCCTAAGATCCCGTCCATCGC-CACTGGGATGGTGGGGCCCTCCTCTTGCTG CTG-GTGGTGGCCCTGGGGATCGGCCTCT-TCATGCGAAGGCGCCACATCGTTCGGAAG CGCACGCTGCGGAGGCTGCTGCAG-GAGAGGGAGCTT

GTGGAGCCTCTTACACCCAGTG-
GAGAAGCTCCCAACCAAGCTCTCTTGAGGATCTTG
AAGGAAACTGAATTCAAAAAGAT-
CAAAGTGCTGGGCTCCGGTGCGTTCGGCACGGTG
TATAAGGGACTCTGGATCCCAGAAGGT-
GAGAAAGTT

AAAATTCCCGTCGCTATCAAGGAATTAA-
GAGAAGCAACATCTCCGAAAGCCAACAAG
GAAATCCTCGATGAAGCCTACGTGATG-
GCCAGCGTGGACAACCCCCACGTGTGCCGC
CTGCTGGGCATCTGCCTCACCTCCACCGTGCAACTC

ATCACGCAGCTCATGCCCTTCGGCTGC-
CTCCTGGACTATGTCCGGGAACACAAAGAC AATAT-
TGGCTCCCAGTACCTGCTCAACTGGTGT-
GTGCAGATCGCAAAGGGCATGAAC
TACTTGGAGGACCGTCGCTTGGTGCAC-
CGCGACCTG

GCAGCCAGGAACGTACTGGTGAAAACAC-
CGCAGCATGTCAAGATCACAGATTTTGGG CTGGC-
CAAACTGCTGGGTGCGGAAGAGAAA-
GAATACCATGCAGAAGGAGGCAAAGT
GCCTATCAAGTGGATGGCATTGGAAT-
CAATTTTACAC

AGAATCTATACCCACCAGAGTGAT-
GTCTGGAGCTACGGGGTGACCGTTTGGGAGTTG
ATGACCTTTGGATCCAAGCCATATGACG-
GAATCCCTGCCAGCGAGATCTCCTCCATCC
TGGAGAAAGGAGAACGCCTCCCTCAGCCACCCATA

TGTACCATCGATGTCTACATGATCATG-
GTCAAGTGCTGGATGATAGACGCAGATAGT CGC-
CCAAAGTTCCGTGAGTTGATCATCGAAT-
TCTCCAAAATGGCCCGAGACCCCCAG
CGCTACCTTGTCATTCAGGGGATGAAAGAATGCAT

TTGCCAAGTCCTACAGACTCCAACTTC-
TACCGTGCCCTGATGGATGAAGAAGACATG GAC-
GACGTGGTGGATGCCGACGAGTACCT-
CATCCCACAGCAGGGCTTCTTCAGCAGC
CCCTCCACGTCACGGACTCCCCTCCTGAGCTCTCTG

AGTGCAACCAGCAACAATTCCACCGTG-
GCTTGCATTGATAGAAATGGGCTGCAAAGC TGTC-
CCATCAAGGAAGACAGCTTCTTGCAGC-
GATACAGCTCAGACCCCACAGGCGCC
TTGACTGAGGACAGCATAGACGACACCT-
TCCTCCCA

GTGCCTGAATACATAAACCAGTCCGTTC-
CCAAAAGGCCCGCTGGCTCTGTGCAGAAT CCT-
GTCTATCACAATCAGCCTCTGAAC-
CCCGCGCCCAGCAGAGACCCACACTACCAGGAC
CCCC

CTCAACACTGTCCAGCCCACCTGTGT-
CAACAGCACATTCGACAGCCCTGCCCACTGG
GCCCAGAAAGGCAGCCACCAAATTAGC-
CTGGACAACCCTGACTACCAGCAGGACTTC TTTC-
CCAAGGAAGCCAAGCCAAATGGCATCTTTAAG

GGCTCCACAGCTGAAAATGCAGAATAC-
CTAAGGGTCGCGCCACAAAGCAGTGAATTT ATTG-
GAGCATGACCACGGAGGATAGTATGAGC-
CCTAAAAAATCCAGACTCTTTCGATA
CCCAGGACCAAGCCACAGCAGGTCCTC-
CATCCCAAC

AGCCATGCCCGCATTAGCTCTTAGAC-
CCACAGACTGGTTTTGCAACGTTTACACCGAC
TAGCCAGGAAGTACTTCCACCTCGGGCA-
CATTTTGGGAAGTTGCATTCCTTTGTCTTC AAACT-
GTGAAGCATTTACAGAAACGCATCCAGCA

AGAATATTGTCCCTTTGAGCAGAAATT-
TATCTTTCAAAGAGGTATATTTGAAAAAAA
AAAAAAAAGTATATGTGAGGATTTTTAT-
TGATTGGGGATCTTGGAGTTTTTCATTGTC GCTAT-
TGATTTTTACTTCAATGGGCTCTTCCAACA

AGGAAGAAGCTTGCTGGTAGCACTTGC-
TACCCTGAGTTCATCCAGGCCCAACTGTGA GCAAG-
GAGCACAAGCCACAAGTCTTCCAGAG-
GATGCTTGATTCCAGTGGTTCTGCTT
CAAGGCTTCCACTGCAAAACACTAAA-
GATCCAAGAA

GGCCTTCATGGCCCCAGCAGGCCG-
GATCGGTACTGTATCAAGTCATGGCAGGTACAG
TAGGATAAGCCACTCTGTCCCTTC-
CTGGGCAAAGAAGAAACGGAGGGGATGAATTCT
TCCTTAGACTTACTTTTGTAAAAATGTCCCCACGGT

ACTTACTCCCCACTGATGGACCAGTG-
GTTTCCAGTCATGAGCGTTAGACTGACTTGTT
TGTCTTCCATTCCATTGTTTTGAAACT-
CAGTATGCCGCCCTGTCTTGCTGTCATGAA
ATCAGCAAGAGAGGATGACACATCAAATAATAAC

TCGGATTCCAGCCCACATTGGATTCAT-
CAGCATTTGGACCAATAGCCCACAGCTGAG AAT-
GTGGAATACCTAAGGATAACAC-
CGCTTTTGTTCTGCAAAAACGTATCTCCTAAT
TTGAGGCTCAGATGAAATGCATCAGGTCCTTTGGG

GCATAGATCAGAAGACTACAAAAAT-
GAAGCTGCTCTGAAATCTCCTTTAGCCATCAC
CCCAACCCCCCAAAATTAGTTTGTGT-
TACTTATGGAAGATAGTTTTCTCCTTTTACTTC ACT-
TCAAAAGCTTTTTACTCAAAGAGTATATGTT

CCCTCCAGGTCAGCTGCCCCCAAAC-
CCCCTCCTTACGCTTTGTCACACAAAAAGTGTC
TCTGCCTTGAGTCATCTATTCAAGCACT-
TACAGCTCTGGCCACAACAGGGCATTTTAC AGGT-
GCGAATGACAGTAGCATTATGAGTAGTGTG

AATTCAGGTAGTAAATATGAAAC-
TAGGGTTTGAAATTGATAATGCTTTCACAACATTT
GCAGATGTTTTAGAAGGAAAAAAGTTC-
CTTCCTAAAATAATTTCTCTACAATTG-
GAAGATTGGA

TCCTAATCTGTGTGTGCCCTGTAACCT-
GACTGGTTAACAGCAGTCCTTTGTAAACAGT GTTT-
TAAACTCTCCTAGTCAATATCCAC-
CCCATCCAATTTATCAAGGAAGAAATGGTT
CAGAAAATATTTTCAGCCTACAGTTATGTTCAGT

CACACACACATACAAAATGTTC-
CTTTTGCTTTTAAAGTAATTTTTGACTCCCAGATCA
GTCAGAGCCCCTACAGCATTGTTAA-
GAAAGTATTTGATTTTTGTCTCAATGAAAATAA
AACTATATTCATTTCC.

The homology observed with the predicted amino acid sequences of v-yes and v-fes was 51 percent and 48 percent, respectively.

Figure 4:
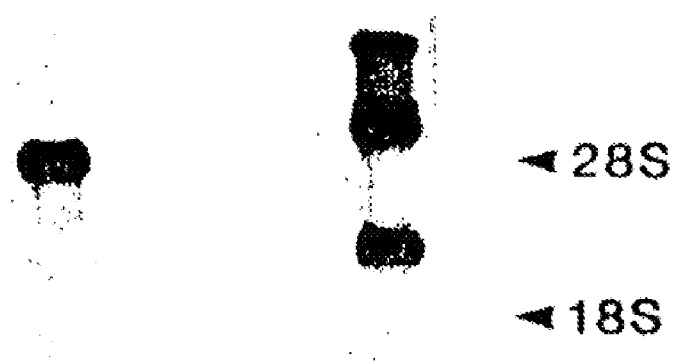

FIG. 4 shows the distinction between λMAC117 and human EGF receptor genes by the detection of distinct messenger RNA species derived from the λMAC117 gene and the human EGF receptor gene. Polyadenylated messenger RNA of A431 cells was separated by denaturing gel electrophoresis in formaldehyde (Lehrach et al., Biochemistry 16:4743, 1977), transferred to nitrocellulose (Southern, J. Mol. Biol. 98:503, 1975), and hybridized under stringent conditions (50 percent formamide, 0.75 M NaCl, 0.075M sodium citrate, at 42° C.) with $^{32}$P-labeled probe from pMAC117 (Bgl I-Bam HI fragment) or human EGF receptor complementary DNA (pE7s 2-kb Cla I inserted fragment). Filters were washed under conditions of high stringency (0.015M NaCl plus 0.0015M sodium citrate at 55° C.). Hybridization was detected by autoradiography with exposure times of 4 hours for the pMAC117 probe and 1 hour for the human EGF receptor probe.

Figure 5:
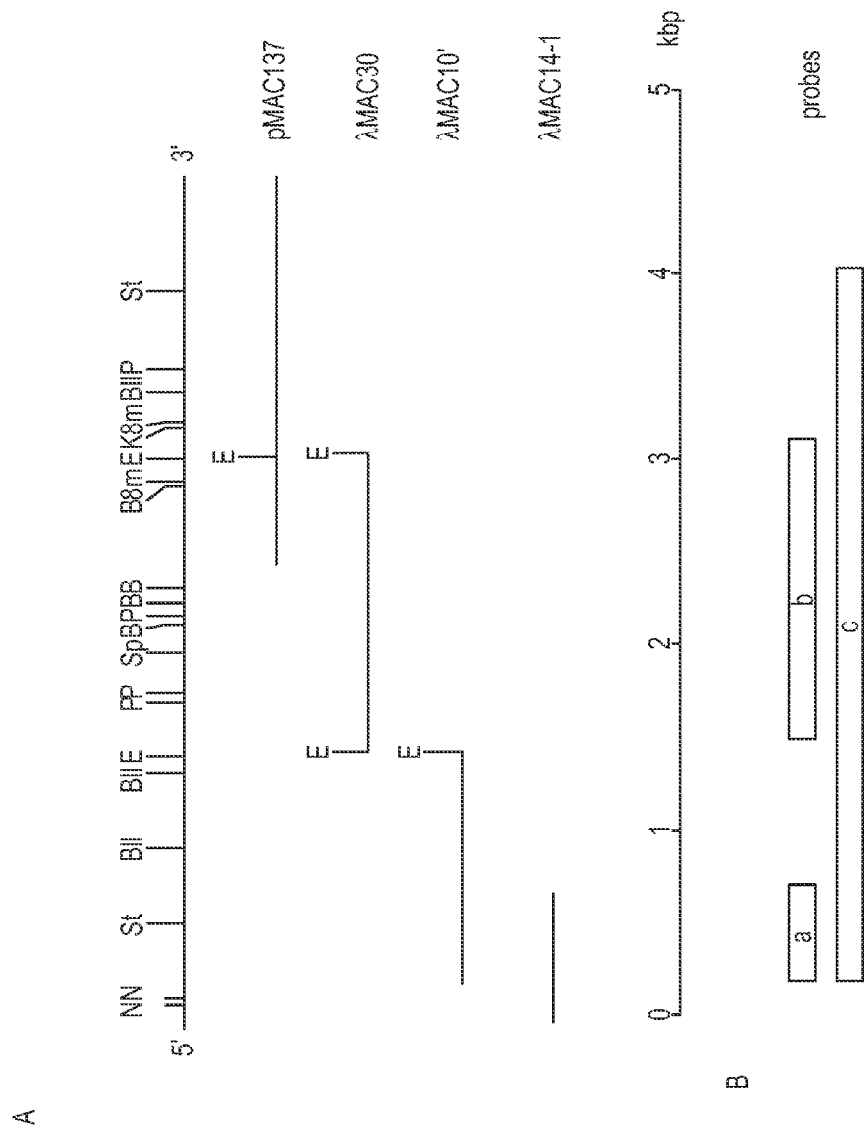

FIG. 5A shows the restriction map of complementary DNA of MAC117 encompassing the entire coding region of the gene. Clone pMAC137 was isolated from an oligo dT primed normal human fibroblast cDNA library (Okyama et al., Mol. Cell. Biol. 3, 280, 1983) using a 0.8-kbp Acc I fragment from the 3' terminus of pMAC117 as probe. Clones λMAC30, λMAC10', and λMAC14-1 were subsequently isolated from a randomly primed MCF-7 cDNA library (Walter et al., Proc. Natl. Acad. Sci. USA, 82, 7889, 1985) using cDNA fragments as probes. Restriction sites: B—Bam HI, BII—Bst EII, E—Eco RI, N—NCO I, P—Pst I, Sm—Sma I, Sp—Sph I, and St—Stu I.

FIG. 5B illustrates three probes, a, b and c, representing the 5' end, a middle portion and the entire coding region, respectively, which were employed in subsequent studies elucidating the role and function of this v-erbB-related gene.

Figure 6:
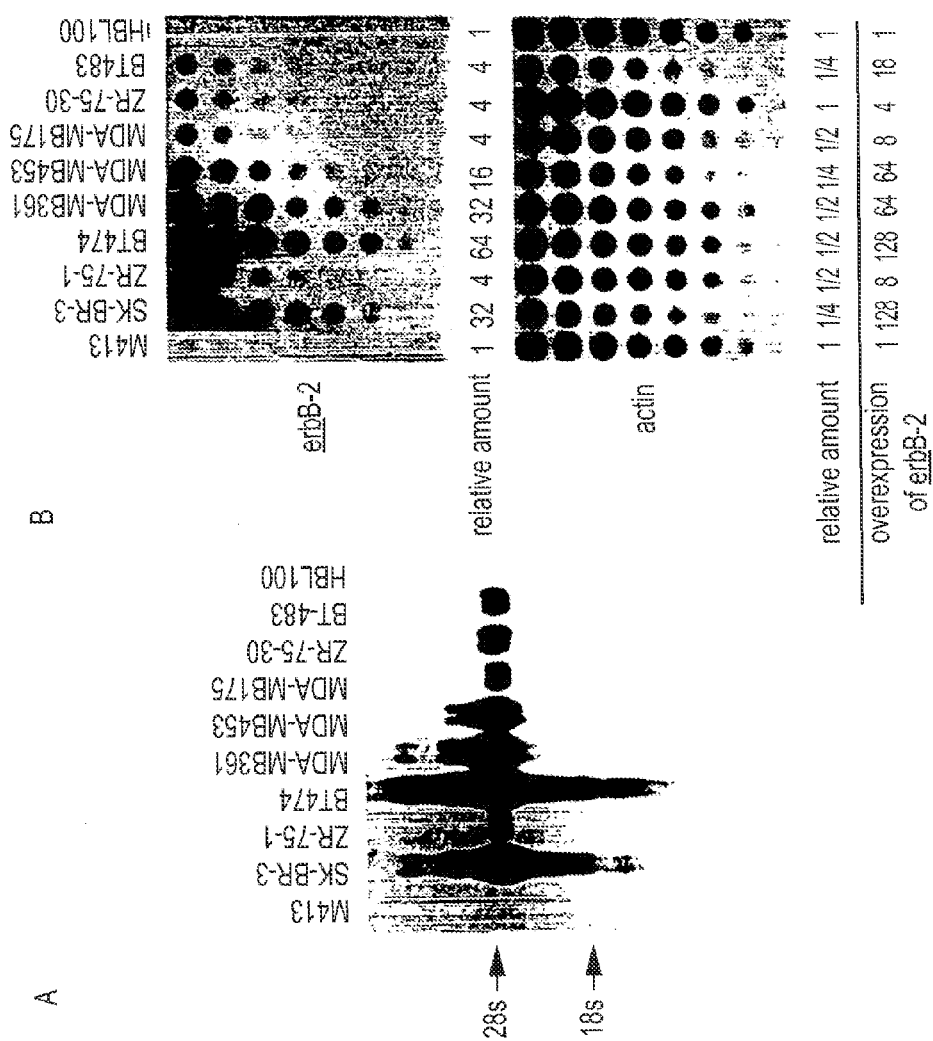

FIG. 6 shows the overexpression of MAC117 in RNA in human mammary tumor cell lines. (A) Northern blot analysis. Total cellular RNA (10 μg) of mammary tumor cell lines, normal fibroblasts M413 and HBL100 was hybridized with a cDNA probe derived from the 5' end of the coding region (FIG. 5B, probe a). M413 and HBL100 cells contain specific mRNA detectable after longer autoradiographic exposures. Similar results were obtained when probe b or c (FIG. 5B) was employed for hybridization. (B) Quantitation of mRNA levels. Serial 2-fold dilutions of total RNA were applied to nitrocellulose. Replicate filters were hybridized with either a cDNA probe (FIG. 5B, probe b) or human β-actin which served as control for RNA amounts present on the nitrocellulose filter. Relative amounts detected with each probe are indicated in comparison to the hybridization signals observed in normal human fibroblast M413.

Figure 7:
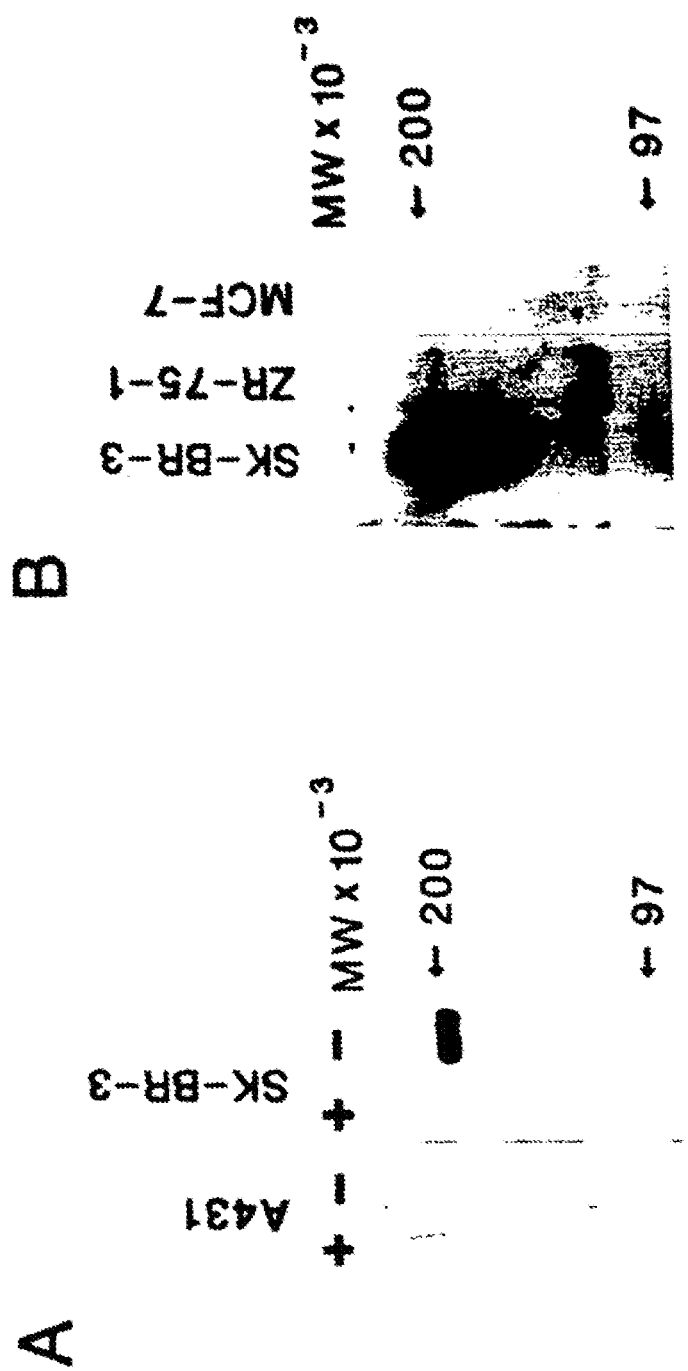

FIG. 7 shows the 185-kDal protein specific for MAC117 and its overexpression in human mammary tumor cell lines. 40 μg total cellulose protein was separated by electrophoresis and transferred to nitrocellulose filters. The protein was detected with an antipeptide antibody coupled to $^{125}$I protein A. The specificity of antibody detection was determined by pre-incubation of the antibody with excess amounts of peptide prior to immunodetection. (+) preincubation with peptide, (−) no peptide. In panel B, nonspecific bands at 100 kd are observed in longer exposures of peptide blocked immunoblots (panel A).

Figure 8:
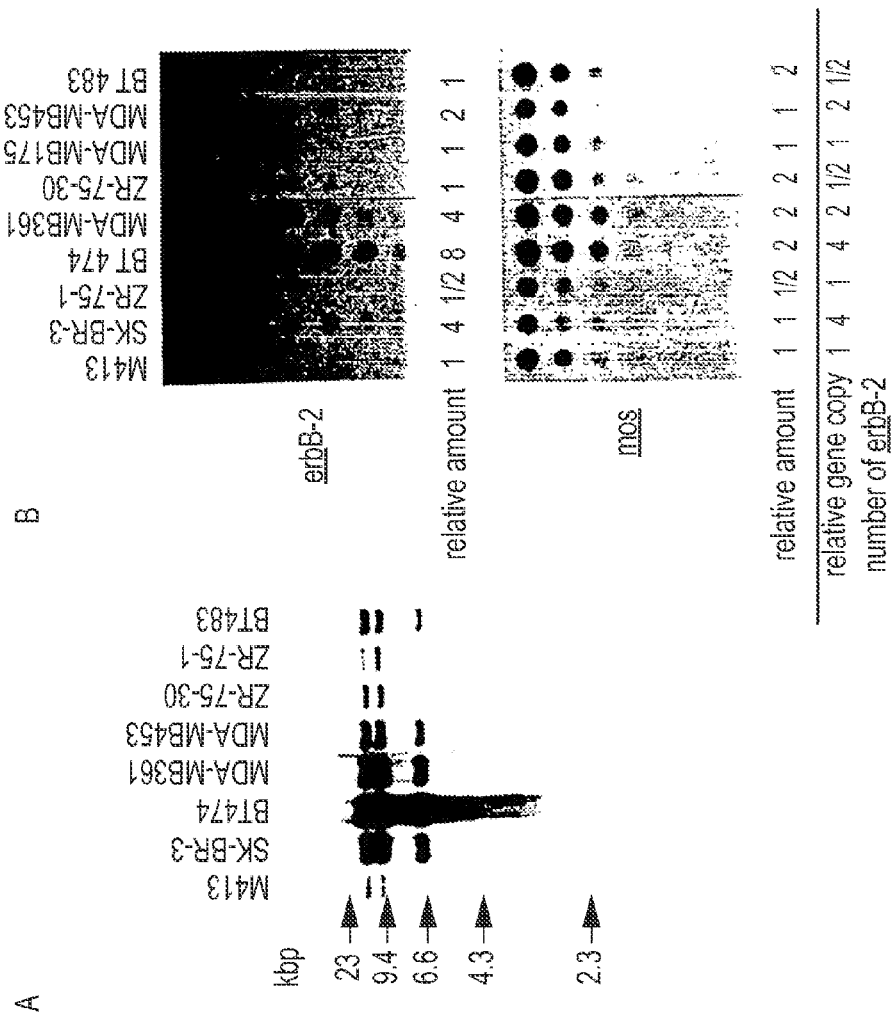

FIG. 8 shows the gene amplification of MAC117 in 4 mammary tumor cell lines and the absence of MAC117 gene amplification in 4 other mammary tumor cell lines overexpressing MAC117 mRNA. (A) Southern blot analysis. For each line 10 μg genomic DNA were restricted with Xba I and hybridized with a probe comprising the entire coding region of MAC117 (FIG. 5B, probe c). Hind III restriction fragments of lambda DNA served as mol. wt. standards. (B) DNA dot-blot analysis. Genomic DNA (10 μg) digested with Eco RI was applied in serial 2-fold dilutions to nitrocellulose filters. Filters were hybridized either with a probe specific for MAC117 (FIG. 5B, probe b) or mos, which served as a control for DNA amounts applied to replicate nitrocellulose filters. Gene copy numbers of MAC117 relative to M413 indicate the minimal extent of gene amplification detected in DNA from mammary tumor cell lines.

Figure 9:
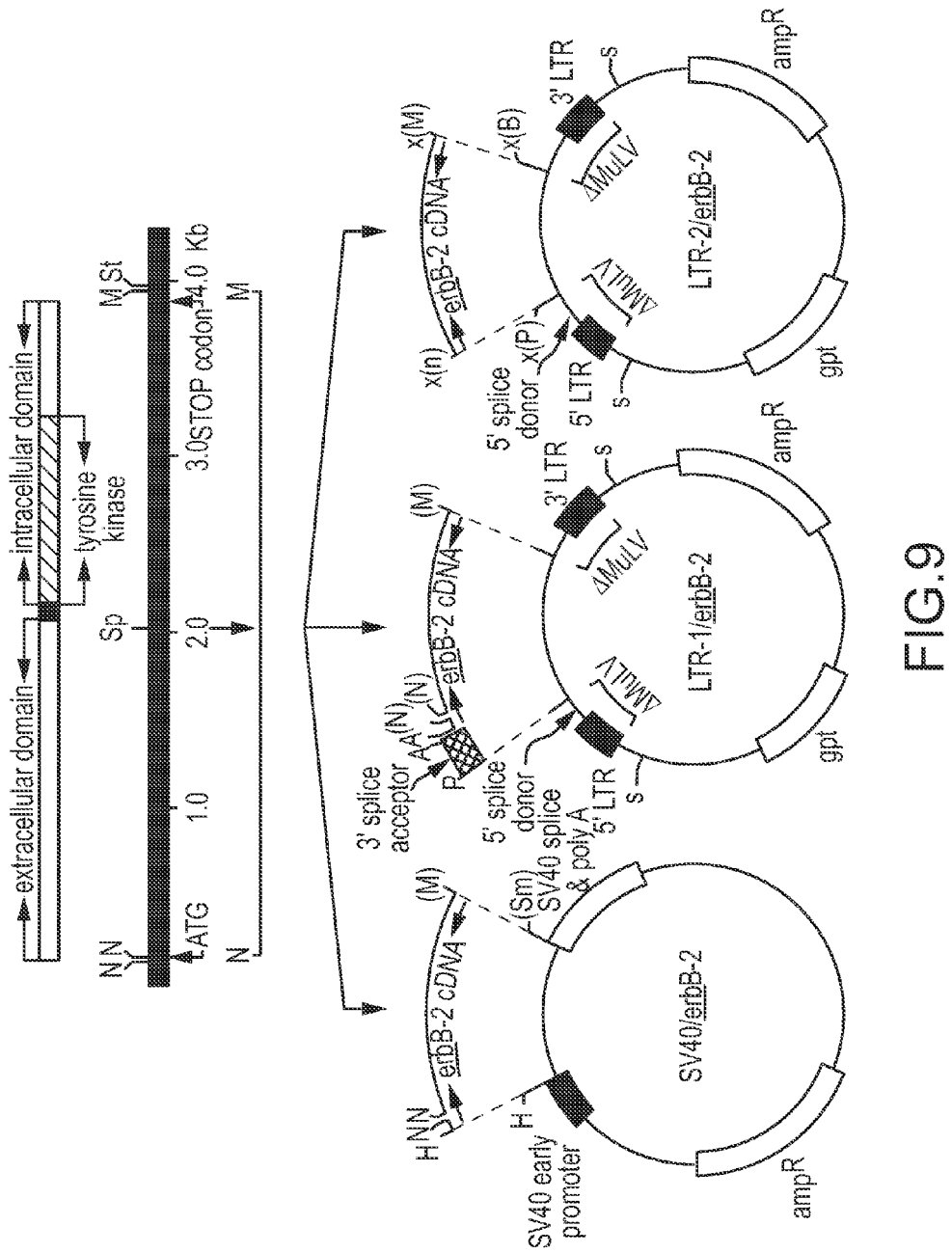

FIG. 9 depicts the construction of expression vectors for the human MAC117 cDNA. A Nco I-Mst II fragment encompassing the entire open reading frame was cloned under the transcriptional control of either the SV40 early promoter or MuLV LTR. Symbols: , erbA-erbB intergenic region of pAEV11 containing the 3' splice acceptor site; N=Nco I, Sp=Sph I, M=Mst II, St=Stu I, H=Hind III, Sm=Sma I, P=Pst I, B=BamH I, X=Xho I. Sites indicated in parenthesis were not reconstituted after the cloning procedures.

Figure 10:
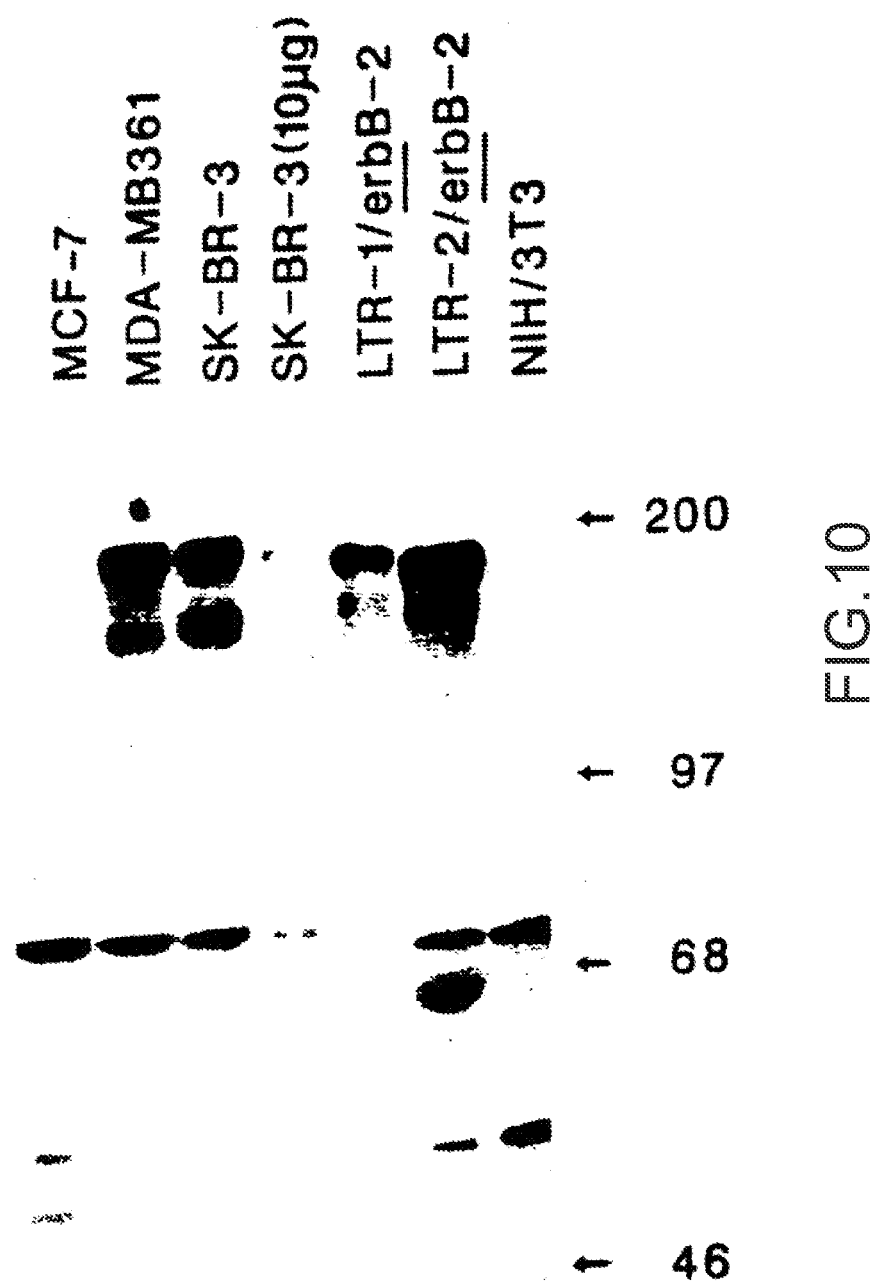

FIG. 10 shows the comparison of the levels of MAC117 proteins in LTR-1/erbB-2 transformed NIH/3T3 cells and human mammary tumor lines by immunoblot analysis. Varying amounts of total cellular protein were separated by electrophoresis and transferred to nitrocellulose filters. The MAC117 protein was detected with rabbit anti-peptide serum coupled to $^{125}$I protein A as previously described.

DETAILED DESCRIPTION OF INVENTION

The above and other objects and advantages of the present invention are achieved by a cloned human gene having the nucleotide sequence as shown in FIG. 1. Although any methods and materials similar or equivalent to those described herein can be used in the practice or testing of the present invention, the preferred methods and materials are now described. All publications mentioned under the "Brief Description of Drawings" and hereunder are incorporated herein by reference. Unless defined otherwise, all technical or scientific terms used herein have the same meaning as commonly understood by one of ordinary skill in the art to which this invention belongs.

Cells and Tissues:
Preparation of High Molecular Weight DNA
1. From A431 cells:

A431 carcinoma cells were established in culture and maintained in Dulbecco's modified Eagle's medium with 10% fetal calf serum.

Cells were grown to 90% confluence in four 175 cm$^2$ tissue culture flasks, washed twice with phosphate buffered saline (Gibco Biochemicals), then lysed in 10 mM Tris (pH 7.5), 150 mM NaCl, 50 mM ethylenediamine-tetraacetate (EDTA) and 0.5% sodium dodecyl sulfate (SDS). Proteinase K (Boehinger Mannheim) was added to a concentration of 0.1 mg/ml and the cell extracts digested for 3 hours at 50° C. DNA was extracted 3 times with phenol and once with CHCl$_3$. DNA was precipitated with 2 volumes of ethanol, spooled and resuspended in 20 ml of 10 mM Tris-HCl (pH 7.5), 1 mM EDTA. The solution was then made 10 μg/ml with (DNase free) RNase (Boehinger Mannheim) and incubated for 2 hr at 50° C. NaCl was added to 0.5 M and the solution extracted with phenol followed by CHCl$_3$. DNA was precipitated with 2 volumes of ethanol, spooled, and resuspended in 10 mM Tris, 1 mM EDTA. The concentration was determined by routine spectrophotometric procedure at 260 nm wavelength.

2. From tissues:

Two grams original mass of primary tumor (designated MAC117 obtained from Memorial Sloan-Kettering Cancer Center Specimen code 31-26606) were pulverized in a mortar and pestle at liquid nitrogen temperature, suspended in 10 ml of 10 mM Tris-HCl (pH 7.5), 150 mM NaCl, 2 mM EDTA, reacted with proteinase K at 500 µg/ml (Boehinger Mannheim) and SDS at 0.5% at 37° C. for 10 hr. The solution was then extracted twice with phenol and twice with the mixture of phenol:CHCl$_3$:isoamyl alcohol at 25:24:1 and once with CHCl$_3$:isoamyl alcohol (24:1). DNA was precipitated by 2 volumes of ethanol removed by spooling, and resuspended in 1 mM Tris-HCl (pH 7.5), 0.2 mM EDTA.

Electrophoretic Analysis of DNA Fragments Using "Southern Hybridization"

1. Restriction Enzyme Cleavage

Each sample of DNA (15 µg) was digested in 0.4 ml of 100 mM Tris-HCl (pH 7.5), 50 mM NaCl, 5 mM MgCl$_2$, 100 ug/ml bovine serum albumin and 30 units of restriction enzyme (New England Biolabs) for 2 hr at 37° C. Following reaction, 10 µg of tRNA was added and the solution extracted once with an equal volume of a mixture of phenol and CHCl$_3$ (1:1). Nucleic acids were precipitated from the aqueous phase by addition of 2 volumes of ethanol. Following centrifugation for 10 min at 12,000×g (Eppendorf microfuge) the samples were washed once with 80% ethanol, dried to remove ethanol, and resuspended in 40 µl distilled H$_2$O.

2. Agarose Gel Electrophoresis

DNA samples were made 40 mM Tris acetate (pH 7.2), 20 mM Na acetate, 1 mM EDTA, 5.0% glycerol, 0.05% bromophenol blue. Electrophoresis was conducted in a BRL H4 apparatus containing 400 ml 0.8% agarose, 40 mM Tris acetate (pH 7.2), 20 mM Na acetate, 1 mM EDTA and 1 µg/ml ethidium bromide for about 16 hr at about 50 volts following conventional procedure. DNA was detected by irradiation with ultraviolet light.

3. Transfer to Nitrocellulose

The agarose gel was treated twice for 15 min in 1 liter of 0.5 M NaOH, 1.5 M NaCl, then twice for 30 min with 1 M NH$_4$Ac, 20 mM NaOH. The agarose gel was then placed on a stack of filter paper saturated with 1 liter of 1 M NH$_4$Ac, 20 mM NaOH. A sheet of nitrocellulose membrane (0.45 µm pore size Schleicher & Schuell) was placed on top of the gel followed by dry filter paper. Transfer was allowed to occur overnight. DNA was fixed to nitrocellulose by baking at 80° C. in vacuo for 2 hr.

Hybridization to RNA and DNA Blots

Hybridization was conducted in 20 ml of 40% formamide, 0.75 M NaCl, 0.075 M Na citrate, 0.05% BSA, 0.05% polyvinyl pyrolidone, 0.05% Ficol 400 and 20 µg/ml sheared denatured calf thymus DNA. All hybridization was conducted for 16 hr at 42° C. in a water bath. Following hybridization, nitrocellulose membranes were washed 2 times for 20 min in 1 liter of 0.3M NaCl, 30 mM Na citrate, followed by washed in 15 mM NaCl, 1.5 mM Na citrate, first with and then without 0.1% sodium dodecyl sulfate. These final washes were at 42° C. for v-erbB probes and at 52° C. with pMAC117 and pE7 probes, vide infra. Autoradiography was conducted at −70° C. with Kodak XAR5 film. Exposure times were 2 hr for FIG. 2A and 20 min for FIG. 2, 40 min for EGF receptor probe on FIG. 4, and 4 hr for the pMAC117 probe of FIG. 4.

Generation of Probe DNAs

A nucleic acid probe is defined as a fragment of DNA or RNA whose nucleotide sequence has at least partial identity with the sequence of the gene or its messenger RNA so as to enable detection or identification of the gene. Since a gene may have several fragments, there could be a plurality of probes for detecting the gene.

The probes used were the 0.5-kb Bam HI to Bam HI fragment combined with the 0.5-kb Bam HI to Eco RI fragment of the v-erbB gene of AEV 11; the 1-kb BglI to Bam HI fragment of pMAC117; and the 2-kb Cla I fragment of pE7 as described by Xu, et al., (*Nature* 309:806, 1984).

DNA fragments were isolated by gel electrophoresis in 1% low melting point agarose gels (Bethesda Research Labs) in 40 mM Tris acetate, 20 mM Na acetate, 1 mm EDTA, followed by melting of the gel at 70° C. and extraction with phenol followed by CHCl$_3$ and ethanol precipitation. DNAs were made radioactive by using a nick-translation kit (Amersham) in which 50 µl reactions contained 250 µCi αP$^{32}$dCTP (Amersham) and 0.5 µg DNA. Radioactive probe DNA was purified from unincorporated nucleotides by 2 cycles of ethanol precipitation. Yields were above 2×10$^8$ cpm/µg DNA. Before hybridization all probes were made single-stranded by treatment with 90% formamide.

RNA Electrophoresis and Transfer to Nitrocellulose

RNA samples (5 µg A431 polyadenylated RNA, obtained from National Institutes of Health, Bethesda, Md. 21218) were treated for 5 min at 50° C. in 50% formamide, 6.7% formaldehyde, 20 mM Mops (pH 7.0) (Sigma Biochemicals), 5 mM Na acetate, 1 mM EDTA in 25 µl total volume. Electrophoresis was conducted in BRL H4 apparatus in 250 ml of 1.5% agarose, 20 mM Mops (pH 7.0), 5 mM Na acetate, 1 mM EDTA, 1 µg/ml ethidium bromide at 40 volts for 16 hr. RNA was detected using ultraviolet light. The gel was soaked for 30 min at 20° C. in 50 mM NaOH, followed by two 30 min washes in 1 M Tris (pH 7.5), followed by 30 min in 3 M NaCl, 0.3 Na citrate. Transfer to nitro-cellulose was accomplished by placing the gel atop a stack of filter paper saturated with 1.5 M NaCl, 0.15 M Na citrate, followed by 0.45 µM pore size nitrocellulose (Schleicher and Schuell), followed by dry filter paper. Transfer was allowed to proceed for 16 hr. The nitrocellulose filter was washed twice for 20 min in 0.3 M NaCl, 30 mM Na citrate. RNA was fixed to the paper by baking at 80° C. in vacuo for 2 hr.

DNA Sequence Analysis

DNA fragments containing the AccI-NcoI region (FIG. 1) were digested with either Nco I, Hinf I or Sau 961 (New England Biolabs). These fragments were end-labeled with reactions of 50 µl containing 50 mM Tris-HCl (pH 7.2), 10 mM MgCl$_2$, 0.1 mM dithiothreitol, 50 µg/ml BSA, 10 µCi α$^{32}$P dxTP (Amersham—where x represents the correct nucleotide for fill-in), 2 units *E. coli* DNA polymerase large fragment (New Englands Biolabs). Following labeling, single-stranded material was prepared by electrophoresis. Samples were denatured in 30% dimethyl sulfoxide, 1 mM EDTA and 0.05% bromophenol blue at 90° C. for 2 hr. Samples were chilled and electrophoresed in acrylamide gels in a Bethesda Research Labs apparatus. DNA was detected by autoradiography and isolated by elution into 10 mM Tris-HCl (pH 7.0), 1 mM EDTA. Chemical degradation of DNA for sequence analysis was conducted using standard procedures. Cleavage at guanine (G) residues was conducted by reaction with dimethyl sulfonate at 22° C. for 10 min. Cleavage at adenine (A) residues was conducted by 12 min reaction at 90° C. in 1.5 M NaOH, 1 mM EDTA. Cleavage at cytosine (C) residues was conducted using hydrazine in 2 M NaCl for 13 min at 22° C. Cleavage at thymine (T) residues was conducted using hydrazine with no added NaCl for 10 min at 22° C. Following cleavage, all reactions were twice precipitated using ethanol and thoroughly dried. All samples were reacted with 1 M piperidine at 90° C. for 30 min. Piperidine was removed by evaporation in a Savant SPEEDVAC concentrator. Fragments were separated by electrophoresis in acrylamide gels (BRL HO apparatus) in 8 M urea, 50 mM Trisborate (pH 8.3), 1 mM EDTA. Detection of degraded ladder was by autoradiography using Kodak XAR5 film at −70° C.

Cloning of λMAC117

High molecular weight DNA (6 μg) from tumor MAC117 (see above) was digested with 12 units restriction enzyme EcoRI (New England Biolabs) in a volume of 100 μl for about one hour at 37° C. DNA was obtained by phenol CHCl$_3$ extraction and ethanol precipitation and resuspended in water at a concentration of 0.1 μg/ml. This DNA (0.2 μg) was ligated to λwes λB arms (Bethesda Research Labs) (1 μg) using T4 DNA Ligase (New England Biolabs) in a total volume of 20 ml [50 mM Tris-HCl pH 7.4, 10 mM MgCl$_2$, 10 mM dithiothreitol, 0.5 mM spermidine, 1 mM ATP]. This mixture of ligated DNAs was packaged into infectious bacteriophage particles using the PACKAGENE system (Promega Biotec). These particles were used to infect bacteria BNN45 and about 8×10$^5$ individual phage plaques were obtained.

These phage plaques were screened for individual plaques containing DNA homologous to the v-erbB probes (described above) using standard procedures. Briefly, bacterial culture plates containing approximately 15,000 plaques were grown overnight. Sterile nitrocellulose discs (Scheicher and Schuell) were applied to the dish, removed and allowed to air dry for about 90 minutes. The discs were then treated with 0.2 M NaOH, 1.5 M NaCl followed by 0.4 M Tris-HCl pH 7.5 followed by 0.3 M NaCl 0.03 M Na citrate and baked in vacuo for two hours at 80° C. These discs were then exposed to hybridization and washing conditions identical to those described for FIG. 2 using the identical v-erbB probe. Washing conditions were also identical to those for FIG. 2. Hybridization was detected by autoradiography at −70° C. for 16 hours. Single hybridizing phage plaques were obtained by three successive hybridization experiments (as described above) to isolate a pure phage culture.

DNA from MAC117 was digested with Eco RI, then ligated into bacteriophage λgtWES, packaged in vitro, and transferred to *Escherichia coli* (*E. coli*) strain BNN45 by infection following standard techniques well known in the art. A library of 4×10$^5$ bacteriophages was screened by plaque hybridization with radioactive v-erbB DNA. Ten of 14 hybridizing phages contained a 6-kbp Eco RI fragment. FIG. 1 shows the physical map of one of these phages, λMAC117, and pMAC117, a PUC12 subclone containing a 2-kbp Bam HI fragment of λMAC117 that hybridized with v-erbB probes. The region of pMAC 117 to which v-erbB hybridized most intensely was flanked by Acc I and Nco I sites. Human repetitive sequences were also localized (FIG. 1, region demarcated by arrows).

A deposit of pMAC117 cloned in *E. coli* has been made at the American Type Culture Collection (ATCC), 10801 University Blvd., Manassas, Va. 20110 under accession number 53408. Upon issuance of a patent, the culture will continue to be maintained for at least 30 years and made available to the public without restriction subject, of course, to the provisions of the law in this respect.

As shown in FIG. 2A, DNA prepared from tissue of a human mammary carcinoma, MAC117, showed a pattern of hybridization that differed both from that observed with DNA of normal human placenta and from that observed with the A431 squamous-cell carcinoma line, which contains amplified epidermal growth factor (EGF) receptor genes. In A431 DNA, four Eco RI fragments were detected that had increased signal intensities compared to those of corresponding fragments in placenta DNA (FIG. 2A). In contrast, MAC117 DNA contained in single 6-kilobase pair (kbp) fragment, which appeared to be amplified compared to corresponding fragments observed in both A431 and placenta DNA's (FIG. 2A). These findings indicate that the MAC117 tumor contained an amplified DNA sequence related to, but distinct from, the cellular erbB proto-oncogene.

By digestion of pMAC117 with Bgl I and Bam HI, it was possible to generate a single-copy probe homologous to v-erbB. This probe detected a 6-kb Eco RI fragment that was amplified in MAC117 DNA and apparently increased in A431 cellular DNA relative to normal DNA (FIG. 2B). The sizes of the fragment corresponded to the amplified 6-kb Eco RI fragment detected in MAC117 DNA by means of v-erbB (FIG. 2A). Hybridization to Southern blots containing serial dilutions of MAC117 genomic DNA indicated an approximate amplification of 5- to 10-fold when compared to human placenta DNA.

The nucleotide sequence of the portion of pMAC117 located between the Nco I and Acc I sites contained two regions of nucleotide sequence homologous to v-erbB separated by 122 nucleotides (FIG. 1). These regions shared 69 percent nucleotide sequence identity with both the v-erbB and the human EGF receptor gene. The predicted amino acid sequence of these regions was 85 percent homologous to two regions that are contiguous in the EGF receptor sequence. Furthermore, these two putative coding regions of the MAC117 sequence were each flanked by the AG and GT dinucleotides that border the exons of eukaryotic genes. These findings suggest that the sequence shown in FIG. 1 represents two exons, separated by an intron of a gene related to the erbB/EGF receptor gene.

Figure 3:
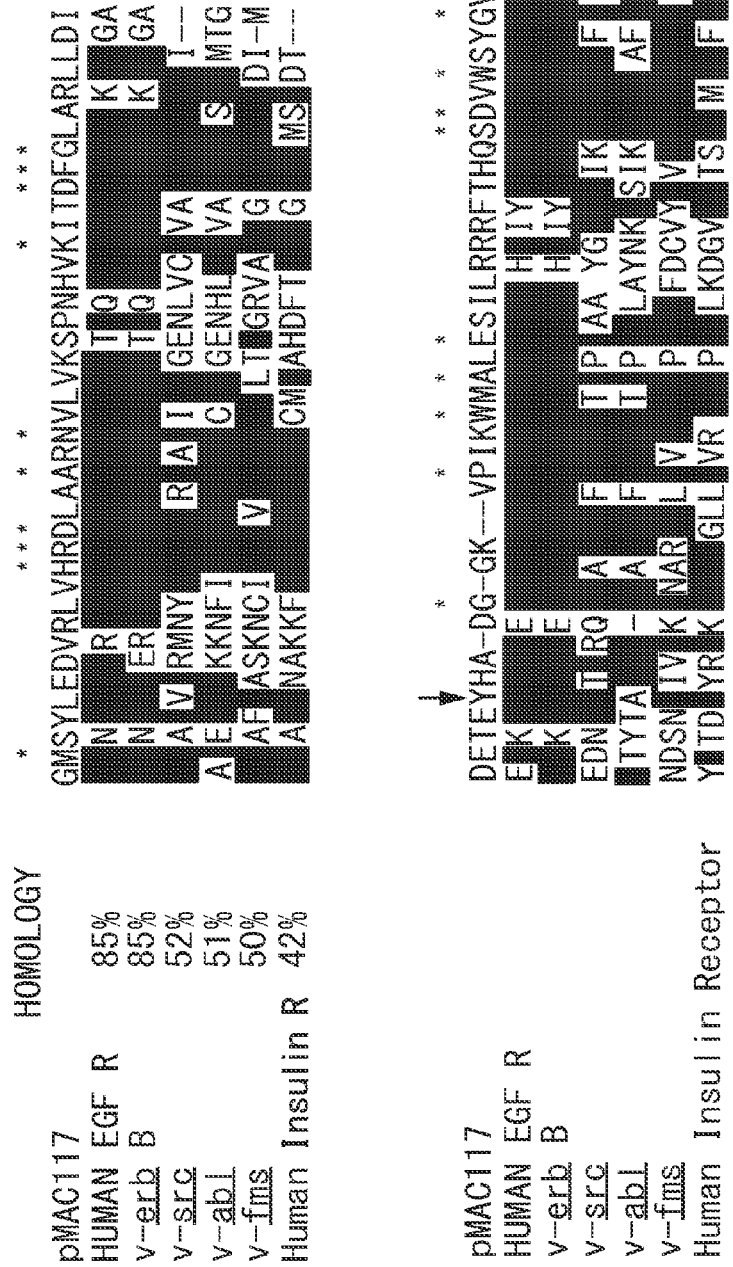
FIG. 3 shows a comparison of the putative encoded amino acid sequence of various polypeptide products, and comparison of the putative encoded amino acid sequence in pMAC117 with known tyrosine kinase sequences. Black regions represent homologous amino acids. Differing amino acid residues are shown in one-letter code (A, alanine; C. cysteine, D. aspartic acid; E. glutamic acid; F. phenylalanine; G. glycine; H. histidine; I. isoleucine; K. lysine; L. leucine; M. methionine; N. asparagine; P. proline; Q. glutamine; R. arginine; S. serine; T. threonine; V. valine; W. tryptophan; Y. tyrosine). Amino acid positions conserved in all sequences are denoted by *. The tyrosine homologous to that autophosphorylated by the v-src protein (Smart et al., Proc. Natl. Acad. Sci. USA 78:6013, 1981) is shown by an arrow. The v-abl sequence contains a tyrosine residue in this region displaced by two positions. The amino acid sequences of human EGF receptor, v-src, v-abl, v-fms, and human insulin receptor were aligned by the computer program described by Ullrich et al., Nature 313:756, 1985 which is incorporated herein by reference.

The predicted amino acid sequence of the λMAC117 putative exons is homologous to the corresponding sequences of several members of the tyrosine kinase family. The most striking homology was observed with the human EGF receptor or erbB (FIG. 3). In addition, 42 percent to 52 percent homology with the predicted amino acid sequences of other tyrosine kinase-encoding genes was observed. At 25 percent of the positions there was identity among all the sequences analyzed (FIG. 3). A tyrosine residue in the λMAC117 putative coding sequence, conserved among the tyrosine kinases analyzed, is the site of autophosphorylation of the src protein (Smart et al., Proc. Natl. Acad. Sci. USA 78:6013, 1981).

The availability of cloned probes of the MAC117 gene made it possible to investigate its expression in a variety of cell types. The MAC117 probe detected a single 5-kb transcript in A431 cells (FIG. 4). Under the stringent conditions of hybridization utilized, this probe did not detect any of the three RNA species recognized by EGF receptor complementary DNA. Provided is a method of detecting amplification of a MAC117 gene, whereint he MAC117 gene contains a nucleotide sequence encoding the amino acids encoded by the 423 nucleotides set forth in FIG. 1, in mammary tissue from said patient by hybridizing a nucleic acid derived from breast tissue of said patient with a nucleic acid probe of the MAC117 gene, the amplification of said MAC117 gene relative to normal human breast tissue indicating the presence of human mammary carcinoma in said patient. Thus, MAC117 represents a new functional gene within the tyrosine kinase family, closely related to, but distinct from the gene encoding the EGF receptor.

There is precedent for the identification of genes related to known oncogenes on the basis of their amplification in human tumors. For example, the high degree of amplification of N-myc in certain malignancies made it detectable by means of the myc gene as a molecular probe (Schwab, Nature 305:245, 1983; Kohl et al., Cell 35:349, 1983). In the present study, a five- to tenfold amplification of a v-erbB-related gene in the MAC117 mammary carcinoma made it possible to identify this sequence against a complex pattern of EFG receptor gene fragments.

The MAC117 coding sequence, as determined by nucleotide and predicted amino acid sequence, is most closely related to the erbB/EGF receptor among known members of the tyrosine kinase family. The two genes are distinct, however, as evidenced by the sequence diversity and transcript size. Detailed structural analysis of the complete coding sequence would further elucidate the role and function of this v-erbB-related gene.

To this purpose we have isolated cDNAs with a complexity of over 4.5 kb from the MAC117 mRNA (Kraus et al., EMBO Journal 6:605-610, 1987). A restriction map is shown in FIG. 5A. An oligo (dT) primed normal human fibroblast cDNA library (Okayama and Berg, 1983) was screened with a 0.8 kbp Acc I DNA fragment from the 3' terminus of a genomic clone of MAC117 (FIG. 1). The largest plasmid obtained, pMAC137, carried a 2-kbp insert comprising 1.5 kbp of 3' coding information and 3' untranslated sequence. The remaining coding information upstream was obtained from three phage clones, λMAC30, λMAC10' and λMAC14-1, identified in a randomly primed MCF-7 cDNA library (Walter et al., 1985; FIG. 5A).

FIG. 5B illustrates 3 probes, a, b, and c, representing the 5' end, a middle portion, and the entire coding region, respectively, which were employed in subsequent studies elucidating the role and function of this v-erbB-related gene.

To assess the role of MAC117 in human mammary neoplasia, we compared mRNAs of 16 mammary tumor cell lines to normal human fibroblasts, M413, and a human mammary epithelial cell line, HBL100. Increased expression of an apparently normal size 5-kb transcript was detected in 8 of 16 tumor cell lines when total cellular RNA was subjected to Northern blot analysis. An aberrantly sized erbB-2 mRNA was not detected in any of the cell lines analyzed (Kraus et al., EMBO Journal 6:605-610, 1987). To quantitate more precisely the amount of MAC117 transcript in eight mammary tumor cell lines which overexpress MAC117, serial 2-fold dilutions of total cellular RNA were subjected to dot blot analysis using β actin as a control for the amount of RNA applied to the nitrocellulose filters. The highest levels of MAC117 mRNA, which ranged from 64- to 128-fold over that of our controls, were observed in the cell lines MDA-MB453, SK-BR-3, MDA-MB361, and BT474. Moreover, MAC117 mRNA levels were increased 4- to 8-fold in four cell lines including BT483, MDA-MB175, ZR-75-30, and ZR-75-1 (FIG. 6).

To determine if the overexpression of MAC117 mRNA resulted in a steady state increase of its encoded gene product, we developed a specific immunoblot assay. Antisera were raised against a synthetic peptide whose sequence corresponded to a portion of the putative tyrosine kinase domain of MAC117. As this region is partially conserved between the encoded proteins of the EGFR and MAC117 genes, we tested its specificity using A431 and SK-BR-3 cell lines which overexpress EGFR or MAC117 mRNA, respectively. As shown in FIG. 7A, a specific band of ~185 kd was detected in extracts of SK-BR-3 but not in A431 cells. This band was not detected when the antibody was preincubated with the synthetic peptide corresponding to its antigen. To estimate the relative amounts of MAC117 protein in different mammary tumor cell lines, immunoblot analysis was conducted using equivalent amounts of total cellular protein. As shown in FIG. 7B, an intense band of protein was detected in extracts of SK-BR-3 and a less intense but readily detectable band in extracts of ZR-75-1. No MAC117 protein was detected in extracts of MCF-7, a mammary tumor cell line, that did not display overexpression of erbB-2 mRNA. We interpret these results to indicate that substantially more erbB-2 protein is found in both SK-BR-3 and ZR-75-1 than in MCF-7 cells where the amount of protein escapes the sensitivity of the assay. These observations indicated that elevated mRNA levels of MAC117 are translated into MAC117 proteins. This demonstrated that gene amplification of MAC117 results in overexpression of mRNA and protein of MAC117 in human mammary tumor cells. Furthermore, increased mRNA and protein levels are observed in mammary tumor cells in the absence of gene amplification suggestive for an additional mechanism as a result of which mRNA and protein of our novel v-erbB-related gene can be found overexpressed in tumor cells (Kraus et al., 1987).

To directly assess the effects of MAC117 overexpression on cell growth properties, we assembled a full length normal human MAC117 clone from overlapping cDNA clones (FIGS. 5A, B) linked to the transcriptional initiation sequences of either the Moloney murine leukemia virus long terminal repeat (MuLV LTR) or the SV40 early promoter in expression vectors in order to express a normal coding sequence of MAC117 in NIH3T3 cells (FIG. 9) (DiFiore et al., Science 237:178-182 1987). Previous studies have indicated different strengths of LTR and the SV40 promoters in these cells (Gorman et al., Proc. Natl. Acad. Sci. USA 79, 6777, 1982). Because of the presence of the MuLV donor splice site close to the 5' LTR (Shinnick et al., Nature 293, 543, 1981), we engineered one of the LTR-based vectors (LTR-1/MAC117) to contain an acceptor splice site immediately upstream of the translation initiation codon of the MAC117 coding sequence (FIG. 9). This vector was constructed in order to ensure correct splicing of the message even if a cryptic splice acceptor site were present within the MAC117 open reading frame. In the SV40-based expression vector (SV40/MAC117) the erbB-2 coding sequence replaced the neomycin-resistance gene of pSV2/neo (Southern et al., J. Mol. Appl. Genet. 1, 327, 1982) (FIG. 9). To assess the biologic activity of our human MAC117 vectors, we transfected NIH/3T3 cells with serial dilutions of each DNA. As shown in Table 1, LTR-1/MAC117 DNAs induced transformed foci at high efficiency of $4.1 \times 10^4$ focus-forming units per picomole of DNA (ffu/pM). In striking contrast, the SV40/erbB-2 construct failed to induce any detectable morphological alteration of NIH/3T3 cells transfected under identical assay conditions (Table 1). Since the SV40/erbB-2 construct lacked transforming activity, these results demonstrated that the higher levels of MAC117 expression under LTR influence correlated with its ability to exert transforming activity. To compare the growth properties of NIH/3T3 cells transfected by these genes, we analyzed the transfectants for anchorage-independent growth in culture, a property of many transformed cells. The colony-forming efficiency of a LTR-1/MAC117 transformant was very high and comparable to that of cells transformed by LTR-driven v-H-ras and v-erbB (Table 1). Moreover, the LTR-1/MAC117 transfectants were as malignant in vivo as cells transformed by the highly potent v-H-ras oncogene and 50-fold more tumorigenic than cells transfected with v-erbB. In contrast, SV40/MAC117 transfectants lacked anchorage-independent growth in vitro and did not grow as tumors in nude mice even when $10^6$ cells were injected (Table 1).

To compare the level of overexpression of the 185-kd protein encoded by MAC117 in human mammary tumor cell lines possessing amplified MAC117 genes with that of NIH/3T3 cells experimentally transformed by the MAC117 coding sequence, we compared MAC117 specific protein amounts by Western blotting (DiFiore et al., Science 237:178-182 1987). An anti-MAC117 peptide serum detected several discrete protein species ranging in size from 150 to 185 kd in extracts of MDA-MB361 and SK-BR-3 mammary tumor cell lines, as well as LTR/MAC117 NIH/3T3 transformants (FIG. 10). The relative levels of the 185-kd MAC117 product were similar in each of the cell lines and markedly elevated over that expressed by MCF-7 cells, where the 185-kd protein was not detectable under these assay conditions (FIG. 10). Thus, human mammary tumor cells which overexpressed the MAC117 gene demonstrated levels of the MAC117 gene product capable of inducing malignant transformation in a model system.

Overexpression of proto-oncogenes can cause cell transformation in culture and may function in the development of human tumors. Amplification of a normal ras gene or its increased expression under the control of a retroviral long terminal repeat (LTR) induces transformation of NIH 3T3 cells (Chang et al., Nature 297:479, 1982). Expression of the normal human sis/PDGF-2 coding sequence in NIH 3T3 cells, which do not normally express their endogenous sis proto-oncogene, also leads to transformation (Gazit et al., Cell 39:89, 1984; Clarke et al., Nature 308:464, 1984). In Burkitt lymphoma, a chromosomal translocation involving myc places its normal coding sequence under the control of an immunoglobulin gene regulatory sequence. The resulting alteration in myc expression is likely to be causally related to tumor development (Nishikura et al., Science 224: 399, 1984). The observation of amplification of myc or N-myc in more malignant phenotypes of certain tumors has supported the idea that overexpression of these genes can contribute to the progression of such tumors. The erbB/EGF receptor gene is amplified or overexpressed in certain tumors or tumor cell lines. The five- or tenfold amplification of the v-erbB-related gene of the present invention in a mammary carcinoma indicates that increased expression of this gene may have provided a selective advantage of this tumor. The isolation of a new member of the tyrosine kinase gene family amplified in a human mammary carcinoma in accordance with the present invention, makes possible the elucidation of the role of this gene in human malignancy.

Use of Specific Nucleic Acid Probes

Figure 2:
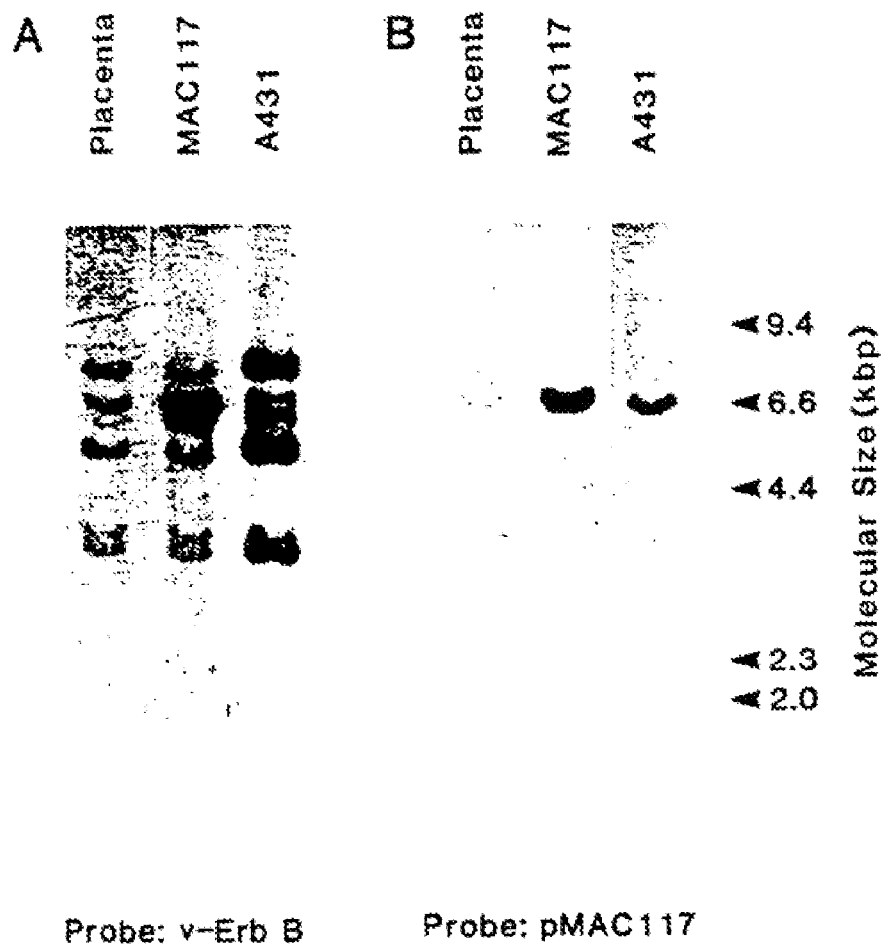
FIG. 2 shows the gel electrophoretic properties of specific gene fragments; detection of v-erbB- and pMAC117-specific gene fragments in normal human placenta, A431 cells or human mammary carcinoma MAC117. DNA (15 μg) was cleaved with Eco RI, separated by electrophoresis in agarose gels and transferred to nitrocellulose paper (Southern, J. Mol. Biol. 98:503 (1975)). Hybridization to the $^{32}$P-labeled probe (Rigby et al., J. Mol. Biol. 113:237 (1977)) was conducted in a solution of 40 percent formamide, 0.75M NaCl and 0.075M sodium citrate at 42° C. (Wahl et al., Proc. Natl. Acad. Sci., USA 76:3693 (1979)). The v-erbB probe (A) was a mixture of the 0.5-kbp Bam HI fragment and the 0.5-kbp Bam HI-Eco RI fragment of avian erythroblastosis proviral DNA. The pMAC117 probe (B) was a 1-kbp Bgl I-Bam HI fragment. After hybridization, the blots were washed first in 0.3M NaCl plus 0.03M sodium citrate at room temperature and then in 0.015M NaCl, 0.0015M sodium citrate and 0.1 percent sodium dodecyl sulfate at 42° C. (v-erbB probed blots) or at 52° C. (pMAC117 probed blots). Hybridization was detected by autoradiography.

As demonstrated in FIGS. 2 and 4, the isolation and use of a Bgl I to Bam HI restriction fragment of pMAC117 to specifically detect the gene and its mRNA product has been set forth. The importance of this technique, involving this probe and others like it, is that the biological functions of the gene described here can be determined and these functions related to practical application, some of which are listed below.

1. Isolation of cloned cDNA. This involves the use of probes specific for the gene described herein; an example is the Bgl I-Bam HI fragment of pMAC117. These probes are made radioactive by standard techniques, such as those noted above, and screening of the libraries of cDNA clones is done using standard methods analogous to those described in "Cloning of λMAC117" above. This approach was employed to clone cDNA comprising the entire coding region of this gene, the restriction map of which is shown in FIG. 5A.

2. Use of cDNA clones. Due to the fact that cDNA clones contain complete information for encoding the protein, these cDNA clones provide a "second generation" of specific probes for the gene described herein. Such probes are shown in FIG. 5B. Their application for hybridization analysis is demonstrated in FIG. 6 and FIG. 8. As shown in FIG. 8, the availability of probes, such as probe B c in FIG. 5B, facilitates the comprehensive hybridization analysis of the entire coding region of this gene or any defined part of it. In addition, the complete coding information allows the expression of the protein product in a heterologous system.

Such systems utilize strong and/or regulated transcription promoters placed in such a way as to direct overexpression of the gene. Techniques for accomplishing expression of the gene are well known in the art and can be found in such publications as Rosenberg et al., Methods in Enzym. 101, 123 (1983); Guarante, L., Methods in Enzym. 101, 181 (1983). The coding region of our novel v-erbB-related gene was overexpressed under the transcriptional control of MuLV-LTR or SV40 early promoter. Thereby, high expression levels were achieved with MuLV-LTR which caused the neoplastic transformation of transfected cells. These cells can be used as a source to rescue infectious recombinant virus which might prove useful to infect heterologous cells not susceptible to DNA transfection. In addition, these cells serve as a source for high and defined levels of antigen for this novel v-erbB-related gene.

3. Preparation of antibodies specific for the protein product of the gene. Of course, the identification and knowledge of the gene allows its product, protein, for example, to be detected. Poly- or monoclonal antibodies are prepared against said protein by standard techniques, often by commercially available services. The critical reagent in the production of antibodies is the antigen (protein) used. In this case, the antigens are either the peptides chemically synthesized by standard and commercially available techniques according to the predicted amino acid sequences derived from the nucleic acid sequence of the gene or its corresponding cDNA. Another potential antigen is the protein itself encoded by the gene and purified from the heterologous expression systems as described above. The antibodies are then employed by standard immunological techniques for the specific detection or diagnostic purposes. Such antibodies were raised against a peptide representing amino acids 35 through 49 of the peptide sequence:

GlyMetSerTyrLeuGluAspValArgLeuValHisArgAspLeuAlaAlaARgAsnValLeuValLysSerProAsn HisValLysIleThrAspPheGlyLeuAlaArgLeuLeuAspIleAspGluThrGluTyrHisAlaAsp GlyGlyLysVal ProIleLysTrpMetAlaLeuGluSerIleLeuArgArgArgPheThrHisGlnSerAspValTrpSerTyrGly (SEQ ID NO:1). The specificity of these antibodies in detecting the gene product of this novel v-erbB-related gene is demonstrated in FIG. 7A. As shown in FIG. 7B and FIG. 10, these antibodies can be utilized to detect the over-expression of the protein product of our novel v-erbB-related gene in human mammary tumor cells.

Further Applications of the Gene:

Having the knowledge of the gene allows preparing specific nucleic acid probes to detect the gene described here or its mRNA product. The probes are, of course, derived from the gene, such as the Bgl I-Bam HI fragment of pMAC117 used in FIGS. 2 and 4, or alternatively such probes are derived from other regions of the gene or its corresponding cDNA corresponding cDNA, as shown in FIG. 5B. The use of nucleic acid probes in the molecular diagnosis of human cancer has been documented (Taub et al., Proc. Natl. Acad. Sci. USA 79, 7837 (1983); Schwab et al., Proc. Natl. Acad. Sci. USA 81, 4940 (1984)). The finding that the gene described here is amplified in a human mammary carcinoma indicates that alterations occur to this gene in human disease. Thus, detection of the amplification or increase expression of this gene provides useful diagnostic tools for the detection and treatment of human mammary carcinoma or other malignancies resulting from the v-erbB related gene. Hence, diagnostic kits which contain as their principal component specific nucleic acid probes for this gene or its mRNA transcript are of commercial value. The probe is used in analyses similar in concept to those shown in FIG. 2 and FIG. 4 for the detection of gene amplification structure or the expression of mRNA.

Specific antibody reagents (as described above) capable of detecting the protein product of the gene described herein are employed in a way similar to the use of specific nucleic acid probes. In other words, the expression of aberrant forms and amounts of a gene product is a measure of the related neoplastic condition (Nishikura et al., Science 224, 399 (1984); Srivastava, et al., Proc. Natl. Acad. Sci. USA 82, 38-42 (1985)). The detection of the aberrant expression of the protein product of the gene is of importance in the diagnosis of human cancers. As shown in FIG. 7 and FIG. 10, antibodies generated against peptides derived from parts of the amino acid sequence:

GlyMetSerTyrLeuGluAspValArgLeuValHisArgAspLeuAlaAlaARgAsnValLeuValLysSerProAsn HisValLysIleThrAspPheGlyLeuAlaArgLeuLeuAspIleAspGluThrGluTyrHisAlaAsp GlyGlyLysVal ProIleLysTrpMetAlaLeuGluSerIleLeuArgArgArgPheThrHisGlnSerAspValTrpSerTyrGly (SEQ ID NO:2) specifically detect the protein product of the gene having the nucleotide sequence:

GTCTACATGGGTGCTTCCCATTCCAGGGGATGAGCTACCTGGAGGATGTGCGGCTCG TACACAGGGACTTGGCCGCTCGGAACGTGCTGGTCAAGAGTCCCAACCATGTCAAAA TTACAGACTTCGGGCTGGCTCGGCTGCTGGACATTGACGAGACAGAGTACCATGCAG ATGGGGGCAAGGTTAGGTGAAGGACCAAGGAGCAGAGGAGGCTGGGTGGAGTGGTG TCTAGCCCATGGGAGAACTCTGAGTGGCCACCTCCCCACAACACACAGTTGGAGGAC TTCCTCTTCTGCCCTCCCAGGTGCCCATCAAGTGGATGGCGCTGGAGTCCATTCTCCG CCGGCGGTTCACCCACCAGAGTGATGTGTGGAGTTATGGTGTGTGATGGGGGGTGTT GGGAGGGGTGGGTGAGGAGCCATGG in human tumor cells. Antibody reagent (produced as described above) is, of course, the critical reagent of the diagnostic kits for this purpose. Such antibody reagents are then employed in such standard methodologies as immunoprecipitation, western blot analysis, immunofluorescence analysis and the like well known in the art. The determination of amplification in a human mammary carcinoma of the gene described here indicates that overexpression (or other abnormality) of the protein product of this gene is functionally important, thus diagnostically relevant. This relevance is further substantiated by the observations that gene amplification of this gene is associated with overexpression of its mRNA and protein in human mammary tumor cells and that protein levels observed in human mammary tumor cell lines exhibiting gene amplification of this gene are sufficient to induce neoplastic transformation of NIH/3T3 cells in vitro. Furthermore, a recent report (Slamon et al., Science 235:177-181, 1987) correlates gene amplification of this novel erbB-related gene with a reduced disease free survival in breast cancer patients, suggesting the potential usefulness of analysis of this gene for its gene product as a diagnostic parameter in the clinical setting management of breast cancer patients.

A diagnostic test in accordance with the present invention involves, for example, material obtained by surgical biopsy of potential tumor material. Such material is then analyzed by one or more procedures as follows.

1. DNA is isolated from the sample by standard methods (see above). The DNA is then analyzed by established methods, such as Southern blot hybridization using standard techniques similar to those used in the analysis shown in FIG. 2. Gene-specific probes (described above) are made radioactive by standard techniques and used for detecting genetic abnormalities. Such abnormalities include gene amplification, as seen in the MAC117 tumor sample and tumor cell lines in FIG. 8, or gene rearrangement, as detected by aberrantly migrating bands of hybridization.

2. RNA is isolated from the tumor sample by standard methods (see above). This RNA is analyzed by blot hybridization techniques similar to those described in FIG. 4. Gene-specific probes (described above) are made radioactive by standard techniques and used for detecting the mRNA products of the erbB-related gene described here. Such abnormalities include overexpression or abnormal forms of RNA. Overexpression of an apparently normal sized mRNA is shown in 8 human mammary tumor cell lines in FIG. 6. In addition, mRNA amount may also be quantitated by spot hybridization procedures in which serial dilutions of RNA are fixed to nitrocellulose filter and the mRNA of v-erbB-related gene described here detected by hybridization. Such a procedure has been employed in FIG. 6B. The foregoing techniques are standard. This allows detection of mRNA overexpression or alteration of structure.

When antigens or proteins (polypeptides) are to be analyzed, the proteins are separated according to molecular size, for example by gel electrophoresis, transferred to nitrocellulose membranes and the protein product of the erbB-related gene described here detected by reaction with specific antibodies, described above. Such a test is able to detect alterations in the quantity of protein as well as abnormal protein forms. With such an approach protein levels of the v-erbB-related gene have been detected in human mammary tumor cell lines (FIG. 7, FIG. 10).

In addition, specific antibodies may be used in the analysis of histological sections. These techniques, which are well known for other antibody specificities, involve the thin sectioning of biopsied material from a potential tumor, followed by reaction with specific antibodies. The antibody-antigen reaction is then made visible by a variety of standard methods including labeling with fluorescently tagged or ferritin tagged second antisera and the like. Such detection systems allow the detection of the localized aberrant display of the protein product of the erbB-related gene described here.

In addition, although the demonstrated genetic abnormality (shown in FIG. 2) of the gene described here occurs in human mammary carcinoma, genetic abnormalities may also be associated with other clinically important syndromes of neoplastic or other origin. Genetic abnormalities have long been known to be involved in thalassemias, for example.

Knowledge of the erbB-related gene described here also makes possible a means of cancer treatment. If it is found that some cancers display abnormally high quantities of the gene product on their surface, such tumors can be treated with antibodies specific for the gene product which have been conjugated to a toxic substance, such as radioactive markers, biological modifiers or toxins and the like. Another treatment modality involves a similar assumption of overexpression. In this approach, a specific natural product, even if unidentified but which has high binding affinity for the protein product of the gene described here is used to target toxins to the tumor cells. This treatment modality is supported by the finding, reported here, of distinct but limited homology of this gene product to the EGF receptor. If a ligand analogous to EGF exists for the erbB-related gene described here, it may serve as such a targeting agent.

Diagnostic kits for the detection of the protein product of the erbB-related gene. Kits useful for the diagnosis of human cancers having abnormalities of this gene are now disclosed.

a) Kits designed to detect the protein by immunoblotting These kits preferably comprise containers containing (a) homogenization solution (50 mM Tris-HCl pH 7.5, 1% sodium dodecyl sulfate and 0.1% β-mercaptoethanol) for the extraction of protein sample from biopsied material from putative tumors; (b) reagents for the preparation of immunoblots of the protein samples (acrylamide gels are prepoured and contain 7.5% acrylamide, 0.025% bis acrylamide, 0.38 M Tris-HCl pH 8.8, 0.1% sodium dodecyl sulfate; the nitrocellulose sheets will be formed to the gel size; and transfer buffer 0.25 M Tris-glycine pH 8.8, 30% methanol); specific antibody reagents for the detection of the protein product of the erbB-related gene (antisera directed against the protein product of erbB-related gene described here and reaction buffer containing 0.1 M Tris-HCl pH 7.5, 5.0 M EDTA, 0.25% gelatin, 0.1% nonidet P-40); and reagents and instructions for the visualization and interpretation of antibody-antigen interaction (these include radioactive protein A; biotin conjugated second antiserum, or peroxidase conjugated second antiserum). While this kit includes components ordinarily found and well known in the art, the critical component is the gene product-specific antibodies and buffers or media for performing immunological tests. The antibodies are derived or prepared as described above from either the peptide sequence predicted from the nucleotide sequence of the gene or its mRNA or from the protein product itself through standard immunization procedures.

b) Kits designed for the detection of the protein product of the erbB-related gene in tissue sections. Such kits include instructions for preparation of sections; instructions and standard reagents for the preparation of slides for microscopy; $H_2O_2$ for removal of endogenous peroxidase; instructions for incubation with antibodies specific for the protein product of the erbB-related gene described here in a buffer solution preferably containing phosphate buffered saline; and second antibodies for detection (these may be coupled to peroxidase, biotin, or ferritin); and instructions for visualization of detection complex. In addition the kits may include: reagents and instructions for the preparation of sections from biopsied putative tumor material; specific antibody reagents for the protein product of erbB-related gene described here and instructions for its reaction with the tissue section; and reagents and instructions for the detection of the protein-antibody interaction either by immunofluorescence, ferritin conjugated second antibodies or other standard methods well known in the art.

A Method for the Treatment of Human Cancers which Express High Levels of the Protein Product of the Gene Described Herein.

This method involves administering to-the patient one of two types of reagent which preferentially binds cells expressing high levels of the protein product of the erbB-related gene described here. These reagents are either antibodies directed against the protein product or a ligand, which is likely to exist because of the homology of the gene to a growth factor receptor. The ligand is isolated by standard techniques using the intrinsic protein kinase activity of the protein product of the erbB-related gene. Extracts of body fluids and cell culture supernatants are incubated with the protein and $\gamma$-$^{32}$PATP. Thus, provided is a method of detecting amplification or increased expression of a MAC117 gene relative to normal human mammary tissue by reacting a body sample from a patient diagnosed with cancer with antibodies having specific binding affinity for a least a portion of the MAC117 protein product. The presence of ligand is inferred by incorporation of $^{32}$P into the protein. The ligand is then purified by standard techniques such as ion exchange chromatography, gel permeation chromatography, isoelectric focusing, gel electrophoresis and the like. The natural ligand or antibody is tagged with one or more agents which will cause injury to cells to which they bind. Such tagging systems include incorporation of radioactive or biological toxins. The present discovery of amplification of the erbB-related gene makes it likely that some tumors carry large amounts of the corresponding protein. Hence, the two type-specific agents will bind in larger amounts to the protein present in the body and thus direct the toxic effects of the reagents to these cells.

It is understood that the examples and embodiments described herein are for illustrative purposes only and that various modifications or changes in light thereof will be suggested to persons skilled in the art and are to be included within the spirit and purview of this application and the scope of the appended claims.

Table 1 compares transformation characteristics of NIH/3T3 cells transfected with vectors generating different expression levels of the MAC117 coding sequence.

TABLE 1

| DNA transfectant[a] | Specific transforming activity[b] (ffu/pM) | Colony-forming efficiency in agar (%)[c] | Cell number required for 50% tumor incidence[d] |
|---|---|---|---|
| LTR-1/MAC117 | $4.1 \times 10^4$ | 45 | $10^3$ |
| SV40/MAC117 | $<10^0$ | <0.01 | $>10^6$ |
| LTR/erbB | $5.0 \times 10^2$ | 20 | $5 \times 10^4$ |
| LTR/ras | $3.6 \times 10^4$ | 35 | $10^3$ |
| pSV2/gpt | $<10^0$ | <0.01 | $>10^6$ |

[a] All transfectants were isolated from plates which received 1 μg cloned DNA and were selected by their ability to grow in the presence of killer HAT medium (Mulligan et al., Proc. Natl. Acad. Sci. USA 78, 2072, 1981).

[b] Focus-forming units were adjusted to ffu/pM of cloned DNA added based on the relative molecular weights of the respective plasmids.

[c] Cells were plated at 10-fold serial dilutions in 0.33% soft agar medium containing 10% calf serum. Visible colonies comprising >100 cells were scored at 14 days.

[d] NFR nude mice were inoculated subcutaneously with each cell line. Ten mice were tested at cell concentrations ranging from $10^6$ to $10^3$ cells/mouse. Tumor formation was monitored at least twice weekly for up to 30 days.

The invention claimed is:

1. A method of identifying the presence of human mammary carcinoma in mammary tissue from a human, said method comprising determining whether a gene that encodes a protein comprising amino acid sequence SEQ ID NO:1 is amplified in said tissue, wherein amplification is present in said tissue when the level of occurrence of the gene in said tissue is greater than the level of occurrence of the gene in normal mammary tissue, wherein amplification of the gene in said mammary tissue from said human relative to normal human mammary tissue is indicative of the presence of human mammary carcinoma in said mammary tissue from said human.

2. The method of claim 1, wherein said gene comprises nucleic acid sequence SEQ ID NO:2.

3. The method of claim 1, wherein said gene encodes a protein comprising the protein encoded by the Bam HI DNA fragment contained in the pUC12 subclone in the *E. coli* strain deposited under ATCC accession number 53408.

4. The method of claim 1, wherein said gene comprises the nucleic acid sequence of the Bam HI DNA fragment contained in the pUC12 subclone in the *E. coli* strain deposited under ATCC accession number 53408.

5. A method of identifying the presence of human mammary carcinoma in mammary tissue from a human, said method comprising analyzing for amplification of DNA of a gene that encodes a protein comprising amino acid sequence SEQ ID NO:1, wherein amplification is present in said tissue when the amount of the DNA of the gene in said tissue is greater than the amount of the DNA of the gene in normal mammary tissue and wherein amplification of the DNA of the gene in said mammary tissue from said human is indicative of the presence of human mammary carcinoma in said mammary tissue from said human.

6. The method of claim 5, wherein said gene comprises nucleic acid sequence SEQ ID NO:2.

7. The method of claim 5, wherein said gene encodes a protein comprising the protein encoded by the Bam HI DNA fragment contained in the pUC12 subclone in the *E. coli* strain deposited under ATCC accession number 53408.

8. The method of claim 5, wherein said gene comprises the nucleic acid sequence of the Bam HI DNA fragment contained in the pUC12 subclone in the *E. coli* strain deposited under ATCC accession number 53408.

9. The method of claim 5, wherein the step of analyzing comprises contacting DNA of the human mammary tissue with a nucleic acid probe that hybridizes to the DNA of the gene that encodes a protein comprising amino acid sequence SEQ ID NO: 1, measuring the amount of the probe that hybridizes to the DNA of the human mammary tissue, and determining that the DNA of the gene is amplified in the mammary tissue from the human when the amount of probe hybridizing to the DNA of the mammary tissue is greater than the amount of probe hybridizing to DNA in normal mammary tissue.

10. The method of claim 5, wherein the step of analyzing comprises isolating DNA from the human mammary tissue and contacting the DNA with a nucleic acid probe that hybridizes to the DNA of the gene that encodes a protein comprising amino acid sequence SEQ ID NO:1, measuring the amount of the probe that hybridizes to the DNA from the human mammary tissue, and determining that the DNA from the gene is amplified in the mammary tissue from the human when the amount of probe hybridizing to the DNA in the mammary tissue is greater than the amount of probe hybridizing to DNA in normal mammary tissue.

11. The method of claim 5, wherein analyzing for amplification of DNA of a gene that encodes a protein comprising amino acid sequence SEQ ID NO:1 is performed by Southern blot analysis.

12. The method of claim 5, further comprising determining whether the gene is overexpressed in the mammary tissue from the human, wherein the overexpression of the gene provides further indication of the presence of human mammary carcinoma in the mammary tissue from the human.

13. The method of claim 12, wherein determining whether the gene is overexpressed in the mammary tissue from the human comprises measuring the level of mRNA encoding a protein comprising amino acid sequence SEQ ID NO:1 in mammary tissue from the human and comparing the measured level to the level of the mRNA occurring in normal mammary tissue.

14. The method of claim 12, wherein determining whether the gene is overexpressed in the mammary tissue from the human comprises measuring the level of a protein comprising amino acid sequence SEQ ID NO:1 in the mammary tissue from the human and comparing the measured level to the level of the protein occurring in normal mammary tissue.

15. The method of claim 14, wherein the level of the protein is measured by reacting an antibody prepared against said protein with said human mammary tissue.

* * * * *

UNITED STATES PATENT AND TRADEMARK OFFICE
CERTIFICATE OF CORRECTION

| | | |
|---|---|---|
| PATENT NO. | : 7,838,216 B1 | Page 1 of 1 |
| APPLICATION NO. | : 07/110791 | |
| DATED | : November 23, 2010 | |
| INVENTOR(S) | : C. Richter King, Matthias H. Kraus and Stuart A. Aaronson | |

It is certified that error appears in the above-identified patent and that said Letters Patent is hereby corrected as shown below:

Column 6, line 32, replace "CGCTTTTGTTCTGCAAAAACGTATCTCCTAAT" with --CGCTTTTGTTCTCGCAAAAACGTATCTCCTAAT--.

Column 7, line 49, replace "cellulose" with --cellular--.

Column 9, line 55, replace the line, "for FIG. 2A and 20 min for FIG. 2, 40 min for EGF receptor" with --for FIG. 2A and 20 min for FIG. 2B, 40 min for EGF receptor--.

Column 10, line 39, replace the word "with" with --in--.

Column 11, line 64, replace the word "in" with --a--.

Column 12, line 47, replace the words "whereint he" with --wherein the--.

Column 15, line 63, replace the words "probe B c in FIG." with --probe c in FIG.--.

Column 16, line 64, replace the word "increase" with --increased--.

Signed and Sealed this
Fifth Day of April, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 78
<212> TYPE: PRT
<213> ORGANISM: Homo sapiens

<400> SEQUENCE: 1

Gly Met Ser Tyr Leu Glu Asp Val Arg Leu Val His Arg Asp Leu Ala
1               5                   10                  15

Ala Arg Asn Val Leu Val Lys Ser Pro Asn His Val Lys Ile Thr Asp
            20                  25                  30

Phe Gly Leu Ala Arg Leu Leu Asp Ile Asp Glu Thr Glu Tyr His Ala
        35                  40                  45

Asp Gly Gly Lys Val Pro Ile Lys Trp Met Ala Leu Glu Ser Ile Leu
    50                  55                  60

Arg Arg Arg Phe Thr His Gln Ser Asp Val Trp Ser Tyr Gly
65                  70                  75

<210> SEQ ID NO 2
<211> LENGTH: 424
<212> TYPE: DNA
<213> ORGANISM: Homo sapiens

<400> SEQUENCE: 2
gtctacatgg gtgcttccca ttccagggga tgagctacct ggaggatgtg cggctcgtac     60
acagggactt ggccgctcgg aacgtgctgg tcaagagtcc caaccatgtc aaaattacag    120
acttcgggct ggctcggctg ctggacattg acgagacaga gtaccatgca gatgggggca    180
aggttaggtg aaggaccaag gagcagagga ggctgggtgg agtggtgtct agcccatggg    240
agaactctga gtggccacct ccccacaaca cacagttgga ggacttcctc ttctgccctc    300
ccaggtgccc atcaagtgga tggcgctgga gtccattctc cgccggcggt tcacccacca    360
gagtgatgtg tggagttatg gtgtgtgatg ggggtgttg ggaggggtgg gtgaggagcc     420
atgg                                                                 424

<210> SEQ ID NO 3
<211> LENGTH: 5532
<212> TYPE: DNA
<213> ORGANISM: Homo sapiens
<220> FEATURE:
<221> NAME/KEY: CDS
<222> LOCATION: (187)..(3816)

<400> SEQUENCE: 3
gccgcgctgc gccggagtcc cgagctagcc ccggcgccgc cgccgcccag accggacgac     60
aggccacctc gtcggcgtcc gcccgagtcc ccgcctcgcc gccaacgcca caaccaccgc    120
gcacggcccc ctgactccgt ccagtattga tcgggagagc cggagcgagc tcttcgggga    180 gcagcg atg cga ccc tcc ggg acg gcc ggg gca gcg ctc ctg gcg ctg       228
       Met Arg Pro Ser Gly Thr Ala Gly Ala Ala Leu Leu Ala Leu
       1               5                   10 ctg gct gcg ctc tgc ccg gcg agt cgg gct ctg gag gaa aag aaa gtt      276
Leu Ala Ala Leu Cys Pro Ala Ser Arg Ala Leu Glu Glu Lys Lys Val
15                  20                  25                  30 tgc caa ggc acg agt aac aag ctc acg cag ttg ggc act ttt gaa gat      324
Cys Gln Gly Thr Ser Asn Lys Leu Thr Gln Leu Gly Thr Phe Glu Asp
                35                  40                  45

```
cat ttt ctc agc ctc cag agg atg ttc aat aac tgt gag gtg gtc ctt    372
His Phe Leu Ser Leu Gln Arg Met Phe Asn Asn Cys Glu Val Val Leu
             50                  55                  60 ggg aat ttg gaa att acc tat gtg cag agg aat tat gat ctt tcc ttc    420
Gly Asn Leu Glu Ile Thr Tyr Val Gln Arg Asn Tyr Asp Leu Ser Phe
         65                  70                  75 tta aag acc atc cag gag gtg gct ggt tat gtc ctc att gcc ctc aac    468
Leu Lys Thr Ile Gln Glu Val Ala Gly Tyr Val Leu Ile Ala Leu Asn
     80                  85                  90 aca gtg gag cga att cct ttg gaa aac ctg cag atc atc aga gga aat    516
Thr Val Glu Arg Ile Pro Leu Glu Asn Leu Gln Ile Ile Arg Gly Asn
 95                 100                 105                 110 atg tac tac gaa aat tcc tat gcc tta gca gtc tta tct aac tat gat    564
Met Tyr Tyr Glu Asn Ser Tyr Ala Leu Ala Val Leu Ser Asn Tyr Asp
                115                 120                 125 gca aat aaa acc gga ctg aag gag ctg ccc atg aga aat tta cag gaa    612
Ala Asn Lys Thr Gly Leu Lys Glu Leu Pro Met Arg Asn Leu Gln Glu
            130                 135                 140 atc ctg cat ggc gcc gtg cgg ttc agc aac aac cct gcc ctg tgc aac    660
Ile Leu His Gly Ala Val Arg Phe Ser Asn Asn Pro Ala Leu Cys Asn
        145                 150                 155 gtg gag agc atc cag tgg cgg gac ata gtc agc agt gac ttt ctc agc    708
Val Glu Ser Ile Gln Trp Arg Asp Ile Val Ser Ser Asp Phe Leu Ser
    160                 165                 170 aac atg tcg atg gac ttc cag aac cac ctg ggc agc tgc caa aag tgt    756
Asn Met Ser Met Asp Phe Gln Asn His Leu Gly Ser Cys Gln Lys Cys
175                 180                 185                 190 gat cca agc tgt ccc aat ggg agc tgc tgg ggt gca gga gag gag aac    804
Asp Pro Ser Cys Pro Asn Gly Ser Cys Trp Gly Ala Gly Glu Glu Asn
                195                 200                 205 tgc cag aaa ctg acc aaa atc atc tgt gcc cag cag tgc tcc ggg cgc    852
Cys Gln Lys Leu Thr Lys Ile Ile Cys Ala Gln Gln Cys Ser Gly Arg
            210                 215                 220 tgc cgt ggc aag tcc ccc agt gac tgc tgc cac aac cag tgt gct gca    900
Cys Arg Gly Lys Ser Pro Ser Asp Cys Cys His Asn Gln Cys Ala Ala
        225                 230                 235 ggc tgc aca ggc ccc cgg gag agc gac tgc ctg gtc tgc cgc aaa ttc    948
Gly Cys Thr Gly Pro Arg Glu Ser Asp Cys Leu Val Cys Arg Lys Phe
    240                 245                 250 cga gac gaa gcc acg tgc aag gac acc tgc ccc cca ctc atg ctc tac    996
Arg Asp Glu Ala Thr Cys Lys Asp Thr Cys Pro Pro Leu Met Leu Tyr
255                 260                 265                 270 aac ccc acc acg tac cag atg gat gtg aac ccc gag ggc aaa tac agc   1044
Asn Pro Thr Thr Tyr Gln Met Asp Val Asn Pro Glu Gly Lys Tyr Ser
                275                 280                 285 ttt ggt gcc acc tgc gtg aag aag tgt ccc cgt aat tat gtg gtg aca   1092
Phe Gly Ala Thr Cys Val Lys Lys Cys Pro Arg Asn Tyr Val Val Thr
            290                 295                 300 gat cac ggc tcg tgc gtc cga gcc tgt ggg gcc gac agc tat gag atg   1140
Asp His Gly Ser Cys Val Arg Ala Cys Gly Ala Asp Ser Tyr Glu Met
        305                 310                 315 gag gaa gac ggc gtc cgc aag tgt aag aag tgc gaa ggg cct tgc cgc   1188
Glu Glu Asp Gly Val Arg Lys Cys Lys Lys Cys Glu Gly Pro Cys Arg
    320                 325                 330 aaa gtg tgt aac gga ata ggt att ggt gaa ttt aaa gac tca ctc tcc   1236
Lys Val Cys Asn Gly Ile Gly Ile Gly Glu Phe Lys Asp Ser Leu Ser
335                 340                 345                 350 ata aat gct acg aat att aaa cac ttc aaa aac tgc acc tcc atc agt   1284
Ile Asn Ala Thr Asn Ile Lys His Phe Lys Asn Cys Thr Ser Ile Ser
```

-continued

```
                  355                 360                 365
ggc gat ctc cac atc ctg ccg gtg gca ttt agg ggt gac tcc ttc aca         1332
Gly Asp Leu His Ile Leu Pro Val Ala Phe Arg Gly Asp Ser Phe Thr
            370                 375                 380 cat act cct cct ctg gat cca cag gaa ctg gat att ctg aaa acc gta         1380
His Thr Pro Pro Leu Asp Pro Gln Glu Leu Asp Ile Leu Lys Thr Val
        385                 390                 395 aag gaa atc aca ggg ttt ttg ctg att cag gct tgg cct gaa aac agg         1428
Lys Glu Ile Thr Gly Phe Leu Leu Ile Gln Ala Trp Pro Glu Asn Arg
    400                 405                 410 acg gac ctc cat gcc ttt gag aac cta gaa atc ata cgc ggc agg acc         1476
Thr Asp Leu His Ala Phe Glu Asn Leu Glu Ile Ile Arg Gly Arg Thr
415                 420                 425                 430 aag caa cat ggt cag ttt tct ctt gca gtc gtc agc ctg aac ata aca         1524
Lys Gln His Gly Gln Phe Ser Leu Ala Val Val Ser Leu Asn Ile Thr
                435                 440                 445 tcc ttg gga tta cgc tcc ctc aag gag ata agt gat gga gat gtg ata         1572
Ser Leu Gly Leu Arg Ser Leu Lys Glu Ile Ser Asp Gly Asp Val Ile
            450                 455                 460 att tca gga aac aaa aat ttg tgc tat gca aat aca ata aac tgg aaa         1620
Ile Ser Gly Asn Lys Asn Leu Cys Tyr Ala Asn Thr Ile Asn Trp Lys
        465                 470                 475 aaa ctg ttt ggg acc tcc ggt cag aaa acc aaa att ata agc aac aga         1668
Lys Leu Phe Gly Thr Ser Gly Gln Lys Thr Lys Ile Ile Ser Asn Arg
    480                 485                 490 ggt gaa aac agc tgc aag gcc aca ggc cag gtc tgc cat gcc ttg tgc         1716
Gly Glu Asn Ser Cys Lys Ala Thr Gly Gln Val Cys His Ala Leu Cys
495                 500                 505                 510 tcc ccc gag ggc tgc tgg ggc ccg gag ccc agg gac tgc gtc tct tgc         1764
Ser Pro Glu Gly Cys Trp Gly Pro Glu Pro Arg Asp Cys Val Ser Cys
                515                 520                 525 cgg aat gtc agc cga ggc agg gaa tgc gtg gac aag tgc aag ctt ctg         1812
Arg Asn Val Ser Arg Gly Arg Glu Cys Val Asp Lys Cys Lys Leu Leu
            530                 535                 540 gag ggt gag cca agg gag ttt gtg gag aac tct gag tgc ata cag tgc         1860
Glu Gly Glu Pro Arg Glu Phe Val Glu Asn Ser Glu Cys Ile Gln Cys
        545                 550                 555 cac cca gag tgc ctg cct cag gcc atg aac atc acc tgc aca gga cgg         1908
His Pro Glu Cys Leu Pro Gln Ala Met Asn Ile Thr Cys Thr Gly Arg
    560                 565                 570 gga cca gac aac tgt atc cag tgt gcc cac tac att gac ggc ccc cac         1956
Gly Pro Asp Asn Cys Ile Gln Cys Ala His Tyr Ile Asp Gly Pro His
575                 580                 585                 590 tgc gtc aag acc tgc ccg gca gga gtc atg gga gaa aac aac acc ctg         2004
Cys Val Lys Thr Cys Pro Ala Gly Val Met Gly Glu Asn Asn Thr Leu
                595                 600                 605 gtc tgg aag tac gca gac gcc ggc cat gtg tgc cac ctg tgc cat cca         2052
Val Trp Lys Tyr Ala Asp Ala Gly His Val Cys His Leu Cys His Pro
            610                 615                 620 aac tgc acc tac gga tgc act ggg cca ggt ctt gaa ggc tgt cca acg         2100
Asn Cys Thr Tyr Gly Cys Thr Gly Pro Gly Leu Glu Gly Cys Pro Thr
        625                 630                 635 aat ggg cct aag atc ccg tcc atc gcc act ggg atg gtg ggg gcc ctc         2148
Asn Gly Pro Lys Ile Pro Ser Ile Ala Thr Gly Met Val Gly Ala Leu
    640                 645                 650 ctc ttg ctg ctg gtg gtg gcc ctg ggg atc ggc ctc ttc atg cga agg         2196
Leu Leu Leu Leu Val Val Ala Leu Gly Ile Gly Leu Phe Met Arg Arg
655                 660                 665                 670 cgc cac atc gtt cgg aag cgc acg ctg cgg agg ctg ctg cag gag agg         2244
```

```
Arg His Ile Val Arg Lys Arg Thr Leu Arg Arg Leu Leu Gln Glu Arg
            675                 680                 685 gag ctt gtg gag cct ctt aca ccc agt gga gaa gct ccc aac caa gct      2292
Glu Leu Val Glu Pro Leu Thr Pro Ser Gly Glu Ala Pro Asn Gln Ala
            690                 695                 700 ctc ttg agg atc ttg aag gaa act gaa ttc aaa aag atc aaa gtg ctg      2340
Leu Leu Arg Ile Leu Lys Glu Thr Glu Phe Lys Lys Ile Lys Val Leu
            705                 710                 715 ggc tcc ggt gcg ttc ggc acg gtg tat aag gga ctc tgg atc cca gaa      2388
Gly Ser Gly Ala Phe Gly Thr Val Tyr Lys Gly Leu Trp Ile Pro Glu
            720                 725                 730 ggt gag aaa gtt aaa att ccc gtc gct atc aag gaa tta aga gaa gca      2436
Gly Glu Lys Val Lys Ile Pro Val Ala Ile Lys Glu Leu Arg Glu Ala
735                 740                 745                 750 aca tct ccg aaa gcc aac aag gaa atc ctc gat gaa gcc tac gtg atg      2484
Thr Ser Pro Lys Ala Asn Lys Glu Ile Leu Asp Glu Ala Tyr Val Met
                755                 760                 765 gcc agc gtg gac aac ccc cac gtg tgc cgc ctg ctg ggc atc tgc ctc      2532
Ala Ser Val Asp Asn Pro His Val Cys Arg Leu Leu Gly Ile Cys Leu
            770                 775                 780 acc tcc acc gtg caa ctc atc acg cag ctc atg ccc ttc ggc tgc ctc      2580
Thr Ser Thr Val Gln Leu Ile Thr Gln Leu Met Pro Phe Gly Cys Leu
            785                 790                 795 ctg gac tat gtc cgg gaa cac aaa gac aat att ggc tcc cag tac ctg      2628
Leu Asp Tyr Val Arg Glu His Lys Asp Asn Ile Gly Ser Gln Tyr Leu
            800                 805                 810 ctc aac tgg tgt gtg cag atc gca aag ggc atg aac tac ttg gag gac      2676
Leu Asn Trp Cys Val Gln Ile Ala Lys Gly Met Asn Tyr Leu Glu Asp
815                 820                 825                 830 cgt cgc ttg gtg cac cgc gac ctg gca gcc agg aac gta ctg gtg aaa      2724
Arg Arg Leu Val His Arg Asp Leu Ala Ala Arg Asn Val Leu Val Lys
                835                 840                 845 aca ccg cag cat gtc aag atc aca gat ttt ggg ctg gcc aaa ctg ctg      2772
Thr Pro Gln His Val Lys Ile Thr Asp Phe Gly Leu Ala Lys Leu Leu
            850                 855                 860 ggt gcg gaa gag aaa gaa tac cat gca gaa gga ggc aaa gtg cct atc      2820
Gly Ala Glu Glu Lys Glu Tyr His Ala Glu Gly Gly Lys Val Pro Ile
            865                 870                 875 aag tgg atg gca ttg gaa tca att tta cac aga atc tat acc cac cag      2868
Lys Trp Met Ala Leu Glu Ser Ile Leu His Arg Ile Tyr Thr His Gln
            880                 885                 890 agt gat gtc tgg agc tac ggg gtg acc gtt tgg gag ttg atg acc ttt      2916
Ser Asp Val Trp Ser Tyr Gly Val Thr Val Trp Glu Leu Met Thr Phe
895                 900                 905                 910 gga tcc aag cca tat gac gga atc cct gcc agc gag atc tcc tcc atc      2964
Gly Ser Lys Pro Tyr Asp Gly Ile Pro Ala Ser Glu Ile Ser Ser Ile
                915                 920                 925 ctg gag aaa gga gaa cgc ctc cct cag cca ccc ata tgt acc atc gat      3012
Leu Glu Lys Gly Glu Arg Leu Pro Gln Pro Pro Ile Cys Thr Ile Asp
            930                 935                 940 gtc tac atg atc atg gtc aag tgc tgg atg ata gac gca gat agt cgc      3060
Val Tyr Met Ile Met Val Lys Cys Trp Met Ile Asp Ala Asp Ser Arg
            945                 950                 955 cca aag ttc cgt gag ttg atc atc gaa ttc tcc aaa atg gcc cga gac      3108
Pro Lys Phe Arg Glu Leu Ile Ile Glu Phe Ser Lys Met Ala Arg Asp
            960                 965                 970 ccc cag cgc tac ctt gtc att cag ggg gat gaa aga atg cat ttg cca      3156
Pro Gln Arg Tyr Leu Val Ile Gln Gly Asp Glu Arg Met His Leu Pro
975                 980                 985                 990
```

```
agt cct aca gac tcc aac ttc tac cgt gcc ctg atg gat gaa gaa gac      3204
Ser Pro Thr Asp Ser Asn Phe Tyr Arg Ala Leu Met Asp Glu Glu Asp
                995                 1000                1005 atg gac gac gtg gtg gat gcc gac gag tac ctc atc cca cag cag          3249
Met Asp Asp Val Val Asp Ala Asp Glu Tyr Leu Ile Pro Gln Gln
        1010                1015                1020 ggc ttc ttc agc agc ccc tcc acg tca cgg act ccc ctc ctg agc          3294
Gly Phe Phe Ser Ser Pro Ser Thr Ser Arg Thr Pro Leu Leu Ser
            1025                1030                1035 tct ctg agt gca acc agc aac aat tcc acc gtg gct tgc att gat          3339
Ser Leu Ser Ala Thr Ser Asn Asn Ser Thr Val Ala Cys Ile Asp
                1040                1045                1050 aga aat ggg ctg caa agc tgt ccc atc aag gaa gac agc ttc ttg          3384
Arg Asn Gly Leu Gln Ser Cys Pro Ile Lys Glu Asp Ser Phe Leu
        1055                1060                1065 cag cga tac agc tca gac ccc aca ggc gcc ttg act gag gac agc          3429
Gln Arg Tyr Ser Ser Asp Pro Thr Gly Ala Leu Thr Glu Asp Ser
            1070                1075                1080 ata gac gac acc ttc ctc cca gtg cct gaa tac ata aac cag tcc          3474
Ile Asp Asp Thr Phe Leu Pro Val Pro Glu Tyr Ile Asn Gln Ser
                1085                1090                1095 gtt ccc aaa agg ccc gct ggc tct gtg cag aat cct gtc tat cac          3519
Val Pro Lys Arg Pro Ala Gly Ser Val Gln Asn Pro Val Tyr His
        1100                1105                1110 aat cag cct ctg aac ccc gcg ccc agc aga gac cca cac tac cag          3564
Asn Gln Pro Leu Asn Pro Ala Pro Ser Arg Asp Pro His Tyr Gln
            1115                1120                1125 gac ccc cac agc act gca gtg ggc aac ccc gag tat ctc aac act          3609
Asp Pro His Ser Thr Ala Val Gly Asn Pro Glu Tyr Leu Asn Thr
                1130                1135                1140 gtc cag ccc acc tgt gtc aac agc aca ttc gac agc cct gcc cac          3654
Val Gln Pro Thr Cys Val Asn Ser Thr Phe Asp Ser Pro Ala His
        1145                1150                1155 tgg gcc cag aaa ggc agc cac caa att agc ctg gac aac cct gac          3699
Trp Ala Gln Lys Gly Ser His Gln Ile Ser Leu Asp Asn Pro Asp
            1160                1165                1170 tac cag cag gac ttc ttt ccc aag gaa gcc aag cca aat ggc atc          3744
Tyr Gln Gln Asp Phe Phe Pro Lys Glu Ala Lys Pro Asn Gly Ile
                1175                1180                1185 ttt aag ggc tcc aca gct gaa aat gca gaa tac cta agg gtc gcg          3789
Phe Lys Gly Ser Thr Ala Glu Asn Ala Glu Tyr Leu Arg Val Ala
        1190                1195                1200 cca caa agc agt gaa ttt att gga gca tgaccacgga ggatagtatg           3836
Pro Gln Ser Ser Glu Phe Ile Gly Ala
            1205                1210 agccctaaaa atccagactc tttcgatacc caggaccaag ccacagcagg tcctccatcc    3896
caacagccat gcccgcatta gctcttagac ccacagactg ttttgcaac gtttacaccg     3956 actagccagg aagtacttcc acctcgggca cattttggga agttgcattc ctttgtcttc   4016
aaactgtgaa gcatttacag aaacgcatcc agcaagaata ttgtcccttt gagcagaaat   4076
ttatctttca aagaggtata tttgaaaaaa aaaaaaaaag tatatgtgag gatttttatt   4136
gattggggat cttggagttt ttcattgtcg ctattgattt ttacttcaat gggctcttcc   4196
aacaaggaag aagcttgctg gtagcacttg ctaccctgag ttcatccagg cccaactgtg   4256
agcaaggagc acaagccaca agtcttccag aggatgcttg attccagtgg ttctgcttca   4316
aggcttccac tgcaaaacac taaagatcca agaaggcctt catggcccca gcaggccgga   4376
tcggtactgt atcaagtcat ggcaggtaca gtaggataag ccactctgtc ccttcctggg   4436
```

-continued

```
caaagaagaa acggagggga tgaattcttc cttagactta cttttgtaaa aatgtcccca   4496
cggtacttac tccccactga tggaccagtg gtttccagtc atgagcgtta gactgacttg   4556
tttgtcttcc attccattgt tttgaaactc agtatgccgc ccctgtcttg ctgtcatgaa   4616
atcagcaaga gaggatgaca catcaaataa taactcggat tccagcccac attggattca   4676
tcagcatttg gaccaatagc ccacagctga gaatgtggaa tacctaagga taacaccgct   4736
tttgttctcg caaaaacgta tctcctaatt tgaggctcag atgaaatgca tcaggtcctt   4796
tggggcatag atcagaagac tacaaaaatg aagctgctct gaaatctcct ttagccatca   4856
ccccaacccc ccaaaattag tttgtgttac ttatggaaga tagttttctc ctttttacttc   4916 acttcaaaag cttttttactc aaagagtata tgttccctcc aggtcagctg cccccaaacc   4976
ccctccttac gctttgtcac acaaaaagtg tctctgcctt gagtcatcta ttcaagcact   5036
tacagctctg gccacaacag ggcatttttac aggtgcgaat gacagtagca ttatgagtag   5096
tgtgaattca ggtagtaaat atgaaactag ggtttgaaat tgataatgct ttcacaacat   5156
ttgcagatgt tttagaagga aaaaagttcc ttcctaaaat aatttctcta caattggaag   5216
attggaagat tcagctagtt aggagcccat ttttttcctaa tctgtgtgtg ccctgtaacc   5276
tgactggtta acagcagtcc tttgtaaaca gtgttttaaa ctctcctagt caatatccac   5336
cccatccaat ttatcaagga agaaatggtt cagaaaatat tttcagccta cagttatgtt   5396
cagtcacaca cacatacaaa atgttccttt tgcttttaaa gtaattttttg actcccagat   5456 cagtcagagc ccctacagca ttgttaagaa agtatttgat ttttgtctca atgaaaataa   5516
aactatattc atttcc                                                  5532
```

<210> SEQ ID NO 4
<211> LENGTH: 1210
<212> TYPE: PRT
<213> ORGANISM: Homo sapiens

<400> SEQUENCE: 4

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
    65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175
```

-continued

```
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
            195                 200                 205
Lys Leu Thr Lys Ile Ile Cys Ala Gln Gln Cys Ser Gly Arg Cys Arg
            210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
            245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Val Thr Asp His
            290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
            325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
            370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
            405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
            485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Lys Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
            565                 570                 575
Asp Asn Cys Ile Gln Cys Ala His Tyr Ile Asp Gly Pro His Cys Val
            580                 585                 590
```

-continued

```
Lys Thr Cys Pro Ala Gly Val Met Gly Glu Asn Asn Thr Leu Val Trp
    595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
        690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005

Asp Val  Val Asp Ala Asp Glu  Tyr Leu Ile Pro Gln  Gln Gly Phe
```

-continued

```
            1010                    1015                    1020
Phe Ser Ser Pro Ser Thr Ser Arg Thr Pro Leu Leu Ser Ser Leu
        1025                1030                1035
Ser Ala Thr Ser Asn Asn Ser Thr Val Ala Cys Ile Asp Arg Asn
        1040                1045                1050
Gly Leu Gln Ser Cys Pro Ile Lys Glu Asp Ser Phe Leu Gln Arg
        1055                1060                1065
Tyr Ser Ser Asp Pro Thr Gly Ala Leu Thr Glu Asp Ser Ile Asp
        1070                1075                1080
Asp Thr Phe Leu Pro Val Pro Glu Tyr Ile Asn Gln Ser Val Pro
        1085                1090                1095
Lys Arg Pro Ala Gly Ser Val Gln Asn Pro Val Tyr His Asn Gln
        1100                1105                1110
Pro Leu Asn Pro Ala Pro Ser Arg Asp Pro His Tyr Gln Asp Pro
        1115                1120                1125
His Ser Thr Ala Val Gly Asn Pro Glu Tyr Leu Asn Thr Val Gln
        1130                1135                1140
Pro Thr Cys Val Asn Ser Thr Phe Asp Ser Pro Ala His Trp Ala
        1145                1150                1155
Gln Lys Gly Ser His Gln Ile Ser Leu Asp Asn Pro Asp Tyr Gln
        1160                1165                1170
Gln Asp Phe Phe Pro Lys Glu Ala Lys Pro Asn Gly Ile Phe Lys
        1175                1180                1185
Gly Ser Thr Ala Glu Asn Ala Glu Tyr Leu Arg Val Ala Pro Gln
        1190                1195                1200
Ser Ser Glu Phe Ile Gly Ala
        1205                1210
```